United States Patent
Myers et al.

(10) Patent No.: US 12,102,731 B2
(45) Date of Patent: Oct. 1, 2024

(54) PORT-ACCESSIBLE MULTIDIRECTIONAL REINFORCED MINIMALLY INVASIVE COLLAGEN DEVICE FOR SOFT TISSUE REPAIR

(71) Applicant: Harbor MedTech, Inc., Lake Forest, CA (US)

(72) Inventors: Keith Elmer Myers, Lake Forest, CA (US); William Jerry Mezger, Coto de Caza, CA (US)

(73) Assignee: Harbor MedTech, Inc., Lake Forest, CA (US)

(*) Notice: Subject to any disclaimer, the term of this patent is extended or adjusted under 35 U.S.C. 154(b) by 355 days.

(21) Appl. No.: 17/245,782

(22) Filed: Apr. 30, 2021

(65) Prior Publication Data

US 2021/0338886 A1 Nov. 4, 2021

Related U.S. Application Data

(60) Provisional application No. 63/122,853, filed on Dec. 8, 2020, provisional application No. 63/019,143, filed on May 1, 2020.

(51) Int. Cl.
*A61F 2/08* (2006.01)
*A61L 27/24* (2006.01)
*C08L 89/06* (2006.01)

(52) U.S. Cl.
CPC ............. *A61L 27/24* (2013.01); *A61F 2/0811* (2013.01); *C08L 89/06* (2013.01);
(Continued)

(58) Field of Classification Search
CPC .................................. A61F 2/08; A61F 2/0063
See application file for complete search history.

(56) References Cited

U.S. PATENT DOCUMENTS

| 4,806,595 A | 2/1989 | Noishiki et al. |
| 5,080,670 A | 1/1992 | Imamura et al. |

(Continued)

FOREIGN PATENT DOCUMENTS

| CA | 2247199 | 9/1997 |
| CN | 108403258 | 8/2018 |

(Continued)

OTHER PUBLICATIONS

Search Report and Written Opinion for International Application No. PCT/US2021/030174 mailed Aug. 3, 2021; 18 pages.

(Continued)

*Primary Examiner* — Melanie R Tyson
*Assistant Examiner* — Cassidy N Stuhlsatz
(74) *Attorney, Agent, or Firm* — Knobbe, Martens, Olson & Bear, LLP

(57) ABSTRACT

Disclosed herein are embodiments of a reinforced collagen matrix device for superior capsule repair. The device can include a collagen matrix cover, a first reinforcement strip positioned along the first side of the cover, and a second reinforcement strip positioned along the second side of the cover. A first end and a second end of the first and second reinforcement strips can extend past the first end and the second end of the collagen matrix cover so as not be covered by the collagen matrix cover. The collagen matrix cover can be folded along a first fold and a second fold and extend over the first and second reinforcement strips so that a portion of the first and second reinforcement strips are covered by the collagen matrix cover along a portion of the length of the first reinforcement strip.

20 Claims, 15 Drawing Sheets

(52) U.S. Cl.
CPC .............. *A61F 2002/0858* (2013.01); *A61F 2220/0075* (2013.01); *A61F 2230/0008* (2013.01); *A61F 2230/0023* (2013.01); *A61F 2230/0026* (2013.01); *A61L 2430/10* (2013.01)

(56) References Cited

U.S. PATENT DOCUMENTS

| | | |
|---|---|---|
| 5,162,430 A | 11/1992 | Rhee et al. |
| 5,264,214 A | 11/1993 | Rhee et al. |
| 5,292,802 A | 3/1994 | Rhee et al. |
| 5,304,595 A | 4/1994 | Rhee et al. |
| 5,306,500 A | 4/1994 | Rhee et al. |
| 5,308,889 A | 5/1994 | Rhee et al. |
| 5,324,775 A | 6/1994 | Rhee et al. |
| 5,328,955 A | 7/1994 | Rhee et al. |
| 5,376,110 A | 12/1994 | Tu et al. |
| 5,376,375 A | 12/1994 | Rhee et al. |
| 5,413,791 A | 5/1995 | Rhee et al. |
| 5,446,091 A | 8/1995 | Rhee et al. |
| 5,470,911 A | 11/1995 | Rhee et al. |
| 5,475,052 A | 12/1995 | Rhee et al. |
| 5,476,666 A | 12/1995 | Rhee et al. |
| 5,510,121 A | 4/1996 | Rhee et al. |
| 5,510,418 A | 4/1996 | Rhee et al. |
| 5,523,348 A | 6/1996 | Rhee et al. |
| 5,527,856 A | 6/1996 | Rhee et al. |
| 5,543,441 A | 8/1996 | Rhee et al. |
| 5,550,187 A | 8/1996 | Rhee et al. |
| 5,550,188 A | 8/1996 | Rhee et al. |
| 5,565,519 A | 10/1996 | Rhee et al. |
| 5,601,557 A | 2/1997 | Hayhurst |
| 5,614,587 A | 3/1997 | Rhee et al. |
| 5,643,464 A | 7/1997 | Rhee et al. |
| 5,728,136 A | 3/1998 | Thal |
| 5,744,545 A | 4/1998 | Rhee et al. |
| 5,786,421 A | 7/1998 | Rhee et al. |
| 5,800,541 A | 9/1998 | Rhee et al. |
| 5,827,937 A | 10/1998 | Agerup |
| 5,866,610 A | 2/1999 | Lang et al. |
| 5,880,242 A | 3/1999 | Hu et al. |
| 5,936,035 A | 8/1999 | Rhee et al. |
| 6,004,333 A * | 12/1999 | Sheffield .......... A61L 31/044 602/44 |
| 6,117,979 A | 9/2000 | Hendriks et al. |
| 6,156,531 A | 12/2000 | Pathak et al. |
| 6,166,184 A | 12/2000 | Hendriks et al. |
| D461,248 S | 8/2002 | Bianchi et al. |
| 6,482,584 B1 | 11/2002 | Mills et al. |
| 6,497,726 B1 | 12/2002 | Carter et al. |
| 6,524,328 B2 | 2/2003 | Levinson |
| 6,544,281 B2 | 4/2003 | ElAttrache et al. |
| 6,613,278 B1 | 9/2003 | Mills et al. |
| 6,616,694 B1 | 9/2003 | Hart |
| 6,629,977 B1 | 10/2003 | Wolf |
| 6,652,818 B1 | 11/2003 | Mills et al. |
| 6,690,659 B1 | 2/2004 | Ahmed et al. |
| 6,746,458 B1 | 6/2004 | Cloud |
| 6,761,735 B2 | 7/2004 | Eberhardt |
| 6,765,896 B1 | 7/2004 | Ahmed et al. |
| 6,805,713 B1 | 10/2004 | Carter et al. |
| 6,863,671 B1 | 3/2005 | Strobel et al. |
| 6,875,216 B2 | 4/2005 | Wolf |
| 6,893,462 B2 | 5/2005 | Buskirk et al. |
| 6,914,126 B2 | 7/2005 | Van Dyke |
| 6,921,412 B1 | 7/2005 | Black et al. |
| 6,936,058 B2 | 8/2005 | Forde et al. |
| 6,947,398 B1 | 9/2005 | Ahmed et al. |
| 6,989,437 B2 | 1/2006 | Van Dyke |
| 7,001,987 B2 | 2/2006 | Van Dyke |
| 7,014,655 B2 | 3/2006 | Barbarash |
| 7,053,051 B2 | 5/2006 | Hendriks et al. |
| 7,090,690 B2 | 8/2006 | Foerster et al. |
| 7,144,413 B2 | 12/2006 | Wilford et al. |
| 7,195,634 B2 | 3/2007 | Schmieding et al. |
| 7,322,986 B2 | 1/2008 | Wolf |
| 7,329,272 B2 | 2/2008 | Burkhart et al. |
| 7,381,213 B2 | 6/2008 | Lizardi |
| 7,479,164 B2 | 1/2009 | Girardot et al. |
| 7,513,910 B2 | 4/2009 | Buskirk et al. |
| 7,579,381 B2 | 8/2009 | Dove |
| 7,704,222 B2 | 4/2010 | Wilk |
| 7,736,327 B2 | 6/2010 | Wilk |
| 7,867,264 B2 | 1/2011 | McDevitt et al. |
| 7,896,913 B2 | 3/2011 | Damm |
| 7,896,915 B2 | 3/2011 | Guyenot |
| 7,914,575 B2 | 3/2011 | Guyenot |
| 7,918,899 B2 | 4/2011 | Girardot et al. |
| 7,993,369 B2 | 8/2011 | Dreyfuss |
| 8,105,379 B2 | 1/2012 | Carter et al. |
| 8,110,001 B2 | 2/2012 | Carter et al. |
| 8,137,411 B2 | 3/2012 | Schankereli |
| 8,142,991 B2 | 3/2012 | Mills et al. |
| 8,153,591 B2 | 4/2012 | Masters et al. |
| 8,167,943 B2 | 5/2012 | Carter et al. |
| 8,343,186 B2 | 1/2013 | Dreyfuss et al. |
| 8,398,694 B2 | 3/2013 | Forde et al. |
| 8,430,909 B2 | 4/2013 | Dreyfuss |
| 8,551,135 B2 | 10/2013 | Kladakis et al. |
| 8,579,922 B2 | 11/2013 | Glick et al. |
| 8,623,052 B2 | 1/2014 | Dreyfuss et al. |
| 8,637,066 B2 | 1/2014 | Binnette et al. |
| 8,663,279 B2 | 3/2014 | Burkhart et al. |
| 8,801,755 B2 | 8/2014 | Dreyfuss et al. |
| 8,821,541 B2 | 9/2014 | Dreyfuss et al. |
| 8,901,078 B2 | 12/2014 | Mezger et al. |
| 8,956,373 B2 | 2/2015 | Ford et al. |
| 8,986,345 B2 | 3/2015 | Denham et al. |
| 9,089,415 B2 | 7/2015 | Brunelle et al. |
| 9,179,907 B2 | 11/2015 | ElAttrache et al. |
| 9,220,808 B2 | 12/2015 | Mezger et al. |
| 9,289,202 B2 | 3/2016 | Martin |
| 9,375,306 B2 | 6/2016 | Sambusseti |
| 9,387,280 B2 | 7/2016 | Brunelle et al. |
| 9,399,084 B2 | 7/2016 | Mezger et al. |
| 9,486,207 B2 | 11/2016 | Dooney, Jr. et al. |
| 9,510,931 B2 | 12/2016 | Hotter et al. |
| 9,592,320 B2 | 3/2017 | Mezger |
| 10,052,091 B2 | 8/2018 | Dreyfuss et al. |
| 10,172,606 B2 | 1/2019 | Sullivan et al. |
| 10,493,180 B2 | 12/2019 | Brunelle et al. |
| 10,507,095 B2 | 12/2019 | Sambusseti |
| 10,611,822 B2 | 4/2020 | Mezger et al. |
| 2001/0018614 A1 | 8/2001 | Bianchi |
| 2001/0031254 A1 | 10/2001 | Bianchi et al. |
| 2002/0055767 A1 | 5/2002 | Forde et al. |
| 2002/0072806 A1 | 6/2002 | Buskirk et al. |
| 2002/0106393 A1 | 8/2002 | Bianchi et al. |
| 2002/0119437 A1 | 8/2002 | Grooms et al. |
| 2003/0023304 A1 | 1/2003 | Carter et al. |
| 2003/0023316 A1 | 1/2003 | Brown et al. |
| 2003/0027125 A1 | 2/2003 | Mills et al. |
| 2003/0097179 A1 | 5/2003 | Carter et al. |
| 2003/0204037 A1 | 10/2003 | Van Dyke |
| 2003/0219486 A1 | 11/2003 | Van Dyke |
| 2003/0224052 A1 | 12/2003 | Van Dyke |
| 2003/0229394 A1 | 12/2003 | Ogle et al. |
| 2004/0059430 A1 | 3/2004 | Kim et al. |
| 2004/0062793 A1 | 4/2004 | Van Dyke |
| 2004/0115172 A1 | 6/2004 | Bianchi et al. |
| 2004/0120910 A1 | 6/2004 | Van Dyke |
| 2004/0138707 A1 | 7/2004 | Greenhalgh |
| 2004/0210308 A1 | 10/2004 | Carter et al. |
| 2004/0253291 A1 | 12/2004 | Girardot et al. |
| 2004/0267362 A1 | 12/2004 | Hwang et al. |
| 2005/0096742 A1 | 5/2005 | Mills et al. |
| 2005/0100862 A1 | 5/2005 | Mills et al. |
| 2005/0101957 A1 | 5/2005 | Buskirk et al. |
| 2005/0119744 A1 | 6/2005 | Buskirk et al. |
| 2005/0136510 A1 | 6/2005 | Hendriks et al. |
| 2005/0249771 A1 | 11/2005 | Malaviya et al. |
| 2006/0029633 A1 | 2/2006 | Kaiser et al. |
| 2006/0073207 A1 | 4/2006 | Masters et al. |
| 2006/0159641 A1 | 7/2006 | Girardot et al. |
| 2006/0193885 A1 | 8/2006 | Leonard Neethling et al. |

(56) References Cited

U.S. PATENT DOCUMENTS

| | | |
|---|---|---|
| 2006/0217804 A1 | 9/2006 | Dove |
| 2006/0217805 A1 | 9/2006 | Dove |
| 2007/0014831 A1 | 1/2007 | Sung et al. |
| 2007/0020225 A1 | 1/2007 | Abramson et al. |
| 2007/0276415 A1 | 11/2007 | Kladakis et al. |
| 2007/0288040 A1* | 12/2007 | Ferree ............... A61F 2/442 606/151 |
| 2008/0051887 A1 | 2/2008 | Carter et al. |
| 2008/0188936 A1 | 8/2008 | Ball et al. |
| 2008/0293637 A1 | 11/2008 | Schroeder et al. |
| 2009/0043337 A1 | 2/2009 | Martin |
| 2009/0130162 A2 | 5/2009 | Pathak et al. |
| 2009/0186333 A1 | 7/2009 | Mills et al. |
| 2009/0204227 A1 | 8/2009 | Derwin et al. |
| 2010/0063541 A1 | 3/2010 | Brunelle et al. |
| 2010/0082104 A1 | 4/2010 | Carter et al. |
| 2010/0099623 A1 | 4/2010 | Schroeder et al. |
| 2010/0099624 A1 | 4/2010 | Schroeder et al. |
| 2010/0143487 A1 | 6/2010 | Masters |
| 2010/0268349 A1 | 10/2010 | Bianchi et al. |
| 2010/0331896 A1 | 12/2010 | Le Couedic et al. |
| 2011/0207671 A1 | 8/2011 | Chang et al. |
| 2011/0221096 A1 | 9/2011 | Schankereli |
| 2011/0224779 A1 | 9/2011 | Schankereli |
| 2011/0301707 A1 | 12/2011 | Buskirk et al. |
| 2012/0010146 A1 | 1/2012 | Han et al. |
| 2012/0041539 A1 | 2/2012 | Masters |
| 2012/0165264 A1 | 6/2012 | Malessa et al. |
| 2012/0271416 A1 | 10/2012 | Mackay |
| 2013/0016156 A1* | 1/2013 | Ooishi ............... C09D 11/54 524/88 |
| 2013/0029915 A1 | 1/2013 | Mezger et al. |
| 2013/0030153 A1 | 1/2013 | Mezger et al. |
| 2013/0030526 A1* | 1/2013 | Mezger ............... A61L 27/58 530/356 |
| 2013/0035721 A1 | 2/2013 | Brunelle |
| 2013/0116799 A1 | 5/2013 | Derwin et al. |
| 2015/0013299 A1 | 1/2015 | Haj-Ali et al. |
| 2015/0025552 A1* | 1/2015 | Stoll ............... A61F 2/0063 606/151 |
| 2015/0065429 A1 | 3/2015 | Mezger et al. |
| 2016/0102134 A1 | 4/2016 | Mezger et al. |
| 2016/0303285 A1 | 10/2016 | Mezger et al. |
| 2017/0143551 A1* | 5/2017 | Coleman ............... A61B 17/04 |
| 2017/0204162 A1 | 7/2017 | Mezger et al. |
| 2018/0078678 A1 | 3/2018 | Derwin et al. |
| 2019/0274675 A1 | 9/2019 | Coleman |
| 2020/0000573 A1* | 1/2020 | Whittaker ............ A61B 17/0483 |
| 2020/0299357 A1 | 9/2020 | Mezger et al. |
| 2022/0280690 A1 | 9/2022 | Myers et al. |

FOREIGN PATENT DOCUMENTS

| | | | |
|---|---|---|---|
| DE | 69722388 | 4/2004 | |
| EP | 0888142 B1 | 5/2003 | |
| EP | 0897942 B1 | 3/2004 | |
| EP | 1410810 | 4/2004 | |
| EP | 0898973 B1 | 1/2005 | |
| FR | 2 800 595 | 5/2001 | |
| HK | 14111225.8 | 11/2014 | |
| IN | 956/DELNP/2014 | 2/2014 | |
| JP | 2000-506050 | 5/2000 | |
| KR | 20170135677 A * | 12/2017 | ............ B01D 15/00 |
| WO | WO 1994/17841 | 8/1994 | |
| WO | WO 97/32615 | 9/1997 | |
| WO | WO 99/27979 | 6/1999 | |
| WO | WO 02/49687 A1 | 6/2002 | |
| WO | WO 2008/142233 | 11/2008 | |
| WO | WO 2009/154344 | 12/2009 | |
| WO | WO 2010/021738 | 2/2010 | |
| WO | WO 2013/016571 A1 | 1/2013 | |
| WO | PCT/US2021/030174 | 4/2021 | |
| WO | WO 2021/222752 | 11/2021 | |

OTHER PUBLICATIONS

U.S. Appl. No. 13/198,534, filed Aug. 4, 2011, Brunelle.

Crea, Alessandro, et al., Treatment of Intrabony Defects Using Guided Tissue Regeneration or Enamel Matrix Derivative: a 3-Year Prospective Randomized Clinical Study, J. Periodontal, Dec. 2008, pp. 2281-2289.

Hu, Kuikui, et al., A Study on the Building of Scaffolds for Skin Tissue Engineering With a Collogen, Acta Academiae Medicnae Jiangzi, 2005, vol. 45, Issue 6.

Nishi, C. et al. 1995 Journal of Biomedical Materials Research 29: 829-834.

Tattini, Jr. et al., Evaluation of shrinkage temperature of bovine pericardium tissue for bioprosthetic heart valve application by differential scanning calorimetry and freeze-drying microscopy, Materials Research Jul. 12, 2006, pp. 1-4, Vo. 10, No. 1.

Zeeman, Raymond, Cross-linking of collagen-based materials, Thesis, University of Twente, Enschede, The Netherlands, 1998, Febodruk BV., The Netherlands.

Zeeman, R., et al., Successive epoxy and carbodiimide cross-linking of dermal sheep collagen, Biomaterial 20 (1999) 921-931.

U.S. Appl. No. 17/684,196, filed Mar. 1, 2022, Reinforced Collagen Device for Soft Tissue Repair.

U.S. Appl. No. 13/560,696 (U.S. Pat. No. 9,220,808), filed Jul. 27, 2012, Crosslinked Human or Animal Tissue Products and Their Methods of Manufacture and Use.

U.S. Appl. No. 13/560,713 (U.S. Pat. No. 8,901,078), filed Jul. 27, 2012, Crosslinked Human or Animal Tissue Products and Their Methods of Manufacture and Use.

U.S. Appl. No. 14/527,571 (U.S. Pat. No. 9,592,320), filed Oct. 29, 2014, Crosslinked Human or Animal Tissue Products and Their Methods of Manufacture and Use.

U.S. Appl. No. 15/422,158 (U.S. Pat. No. 10,611,822), filed Feb. 1, 2017, Crosslinked Human or Animal Tissue Products and Their Methods of Manufacture and Use.

U.S. Appl. No. 16/834,824, filed Mar. 30, 2020, Crosslinked Human or Animal Tissue Products and Their Methods of Manufacture and Use.

U.S. Appl. No. 13/560,757 (U.S. Pat. No. 9,399,084), filed Jul. 26, 2016, Crosslinked Human or Animal Tissue Products and Their Methods of Manufacture and Use.

U.S. Appl. No. 63/122,853, filed Dec. 8, 2020, Port-Accessible Multidirectional Reinforced Minimally Invasive Collagen Device for Soft Tissue Repair.

U.S. Appl. No. 63/155,630, filed Mar. 2, 2021, Reinforced Collagen Device for Soft Tissue Repair.

U.S. Appl. No. 14/527,570 (U.S. Pat. No. 9,592,320), filed Oct. 29, 2014, Crosslinked Human or Animal Tissue Products and Their Methods of Manufacture and Use.

U.S. Appl. No. 15/422,158 (U.S. Pat. No. 10,611,822), filed Apr. 7, 2020, Crosslinked Human or Animal Tissue Products and Their Methods of Manufacture and Use.

U.S. Appl. No. 13/560,757 (U.S. Pat. No. 9,399,084), filed Jul. 27, 2012, Crosslinked Human or Animal Tissue Products and Their Methods of Manufacture and Use.

* cited by examiner

PORT-ACCESSIBLE MULTIDIRECTIONAL REINFORCED MINIMALLY INVASIVE COLLAGEN DEVICE FOR SOFT TISSUE REPAIR

PRIORITY CLAIM AND INCORPORATION BY REFERENCE

The present application claims the benefit under 35 U.S.C. § 119(e) to U.S. Patent Application No. 63/019,143, filed on May 1, 2020 and U.S. Patent Application No. 63/122,853, filed on Dec. 8, 2020, the contents of each of these priority applications are hereby incorporated by reference herein in their entirety as if fully set forth herein for all purposes. Any and all applications for which a foreign or domestic priority claim is identified in the Application Data Sheet as filed with the present application are hereby incorporated by reference herein in their entirety and made a part of this specification.

BACKGROUND

Field of the Disclosure

The present disclosure relates to devices and methods for repair of tendons of the joints and other connective tissue, for example and without limitation, endoscopic repair of tendons of the joints and other connective tissue.

Description of the Related Art

Massive rotator cuff tear has a very high instance of occurrence in rotator cuff injuries. For example, approximately 40% of all rotator cuff injuries have a massive rotator cuff tear. If such injuries are not treated in a timely manner, atrophy typically results in progressive irreparable damage to the structure of the shoulder. Similarly, such damage can occur as well in tendon tears in other joints and structures of the human body.

The Superior Capsule is a tendon located under the rotator cuff above the shoulder joint. Continued loading of the joint after a massive rotator cuff tear often results in an overload to the Superior Capsule, typically resulting in irreparable damage.

Current surgical techniques include endoscopic placement of collagen based materials in an attempt help promote healing of the tendon. Problems with all collagen matrices are their limited tensile strength however. This is especially a factor at the materials fixation point to bone and other tendinous structures.

SUMMARY OF SOME EXEMPLIFYING EMBODIMENTS

Embodiments of the present disclosure are configured for endoscopic reconstruction of the shoulder and, in some embodiments, for endoscopic reconstruction of the Superior Capsule (SC) after a massive rotator cuff tear with subsequent SC failure.

The current most promising techniques include using bone screws and the combination of bone anchors and sutures to fix a collagen patch to the boney structure. This results in an inherent weakness due to potential tearing at the anchor points and cheese wire effect and abrasion at the suture tie down locations.

Some embodiments of the devices and methods for treatment of the shoulder joint, including without limitation, the SC, disclosed herein comprise a device that augments a collagen patch of human or animal origin using a polymeric surgical mesh material located at appropriate lines of mechanical rotational and vector stresses as well to provide an abrasion resistant and a strong and durable stress absorbing site for anchor placement in bone. To avoid biological irritation and reaction, some embodiments of the device have a polymeric load bearing material covered with Collagen material (preferably of Type I collagen). In some embodiments, the collagen can be configured to cover all polymeric reinforcement material surfaces that are exposed in the joint in order to lower the potential for foreign body inflammation and abrasion from the joint tissue and to lower the potential for direct contact of body fluids with the polymeric fibers.

Without limitation, some embodiments of the device, such as those intended for superior capsule repair (SCR), sometimes also referred to as superior capsule reconstruction, can have a trapezoidal shape and can have reinforcing fibers on the lateral sides of the implant. Long extending tails of the fiber reinforcement can be used to locate the device through an endoscopic surgical port, for example a surgical port of an approximately 12 mm diameter. Using endoscopic techniques, the four reinforced corners of the patch can be inserted into the joint cavity and adjusted to align with the intended anchor location and potential lines of anatomic stresses. The reinforced device can be anchored into the boney structure of the joint using bone screws, bone anchors, or any other attachment devices or components. In some embodiments, insertion of the collagen material into the bone hole, which can be compressed using the screw or anchor, is intended to induce cellular ingrowth directly into the collagen/fabric matrix. This can result in a long-term permanent anchor of the repair.

Disclosed herein are embodiments of a reinforced collagen matrix device that can be used for superior capsule repair. In any embodiments disclosed herein, the embodiments of the reinforced collagen matrix device can include a collagen matrix cover having a length extending between a first end and a second end, a first fold adjacent to a first lateral side edge, and a second fold adjacent to a second lateral side edge, a first reinforcement strip (which, in any embodiments disclosed herein, can comprise a mesh material) positioned along the first lateral side edge and a second reinforcement strip (which, in any embodiments disclosed herein, can comprise a mesh material) positioned along the second lateral side edge. In any embodiments disclosed herein, without limitation, the apparatus can be fixed in position with either sutures, anchors, or both sutures and anchors.

In some embodiments, the first reinforcement strip can include a first surface and an opposite second surface, and the second reinforcement strip can include a first surface and an opposite second surface. Further, the first reinforcement strip can have a length that is greater than the length of the collagen matrix cover such that a first end and a second end of the first reinforcement strip extend past the first end and the second end of the collagen matrix cover and are not covered by the collagen matrix cover, and the first reinforcement strip can have a width that is substantially greater than a thickness of the first reinforcement strip. Further, in any embodiments disclosed herein, the collagen matrix cover can be folded along the first fold and can extend over the first reinforcement strip so that the first surface and the second surface of the first reinforcement strip are covered by the collagen matrix cover along a portion of the length of the first reinforcement strip. Similarly, the second reinforcement strip can have a length that is greater than the length of the collagen matrix cover such that a first end and a second end of the second reinforcement strip extend past the first and the second ends of the collagen matrix cover and are not covered by the collagen matrix cover, and the second reinforcement strip can have a width that is substantially greater than a thickness of the second reinforcement strip. Further, the collagen matrix cover can be folded along the second fold and can extend over the second reinforcement strip so that the first surface and the second surface of the second reinforcement strip are covered by the collagen matrix cover along a portion of the length of the second reinforcement strip.

Any embodiments of a reinforced collagen matrix device, methods of using any of the embodiments of the reinforced collagen matrix devices, and/or any other devices or methods disclosed herein can include, in additional embodiments, one or more of the following steps, features, components, and/or details, in any combination with any of the other steps, features, components, and/or details of any other embodiments disclosed herein: wherein the collagen matrix cover can include a collagen material; wherein the collagen matrix cover can have trapezoidal shape after folding along the first and second folds; further including at least four bone anchors, wherein the reinforced collagen matrix device can be configured to be anchored to the patient using the at least four bone anchors, and wherein one bone anchor can be used for each of the first end portion of the first reinforcement strip, the second end portion of the first reinforcement strip, the first end portion of the second reinforcement strip, and the second end portion of the second reinforcement strip; including a first suture coupling the first reinforcement strip to the collagen matrix cover, the first suture extending through the collagen matrix cover and the first reinforcement strip; wherein the first suture extends through two layers of the collagen matrix cover and the first reinforcement strip that is positioned between the two layers of the collagen matrix cover; wherein the first suture can include multiple lines of sutures extending along the length of the collagen matrix cover; including a second suture coupling the second reinforcement strip to the collagen matrix cover, the second suture extending through the collagen matrix cover and the second reinforcement strip; wherein the second suture extends through two layers of the collagen matrix cover and the second reinforcement strip that is positioned between the two layers of the collagen matrix cover; wherein the second suture can include multiple lines of sutures extending along the length of the collagen matrix cover; and/or wherein the reinforcement strip can include a polymeric surgical mesh material; wherein the reinforcement strips are longer than the collagen matrix cover.

Any embodiments of a reinforced collagen matrix device, methods of using any of the embodiments of the reinforced collagen matrix devices, and/or any other devices or methods disclosed herein can include, in additional embodiments, one or more of the following steps, features, components, and/or details, in any combination with any of the other steps, features, components, and/or details of any other embodiments disclosed herein: wherein the reinforced collagen matrix device can be configured to cover any joint or sliding tendinous structure; wherein the collagen matrix cover can have a trapezoidal or rectangular shape; wherein the collagen matrix cover can have an ovoidal shape; wherein the collagen matrix cover can have a triangular shape; wherein the collagen matrix cover can be configured to be cut in an anatomical shape to match a shape of a natural tendinous structure requiring surgical repair; wherein the reinforcement strip includes a mesh material; wherein the collagen matrix cover covers an entire periphery of the first and second reinforcement strips along a length of the first and the second reinforcement strips that overlap the collagen matrix cover; wherein the collagen matrix cover has a first end edge that is approximately 1.6 times longer than a second, opposite end edge; wherein the collagen matrix cover has a first side edge that is approximately 1.6 times longer than the first end edge; wherein the reinforcement strip includes at least one of a thread, a suture, a sheet, a strip, a fabric, and a weave; wherein the collagen matrix cover includes at least one channel or cut having a reduced thickness along at least the first fold, the reduced thickness being less than a thickness of the collagen matrix cover adjacent to the at least one channel; wherein the collagen matrix cover includes at least one channel or cut having a reduced thickness along at least the first fold, wherein the reduced thickness is approximately 0.1 mm, and the thickness of the collagen matrix cover adjacent to the at least one channel is approximately 0.5 mm; wherein the reduced thickness of the channel is from 10% to 50% of the thickness of the collagen matrix cover adjacent to the at least one channel; wherein the reduced thickness of the channel is from 15% to 30% of the thickness of the collagen matrix cover adjacent to the at least one channel; and/or wherein the reinforcement strip includes a braided material; and/or wherein the reinforcement strip includes a mesh material.

Any embodiments of a reinforced collagen matrix device, methods of using any of the embodiments of the reinforced collagen matrix devices, and/or any other devices or methods disclosed herein can include, in additional embodiments, one or more of the following steps, features, components, and/or details, in any combination with any of the other steps, features, components, and/or details of any other embodiments disclosed herein: wherein the collagen matrix cover includes: a collagenous substrate comprising collagen strands, a crosslink, and a quenched crosslinking agent; wherein the crosslink includes a crosslinking unit, a first amine, and a second amine, the first amine being part of a first collagen strand of the collagenous substrate and the second amine being part of a second collagen strand of the collagenous substrate, the crosslink being represented by Formula (I):

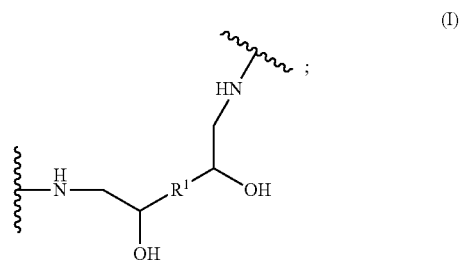

wherein the quenched crosslinking agent is bonded to the collagenous material through a third amine of the collagenous substrate and is represented by Formula (II); wherein R1 is selected from the group consisting of optionally substituted alkylene, optionally substituted polyether, and optionally substituted polyamino; wherein $R^2$ is selected from the group consisting of optionally substituted alkylene, optionally substituted polyether, and optionally substituted polyamino; wherein X1 is selected from the group consisting of —O— and —NH—;

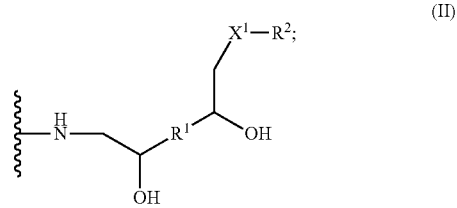

(II)

wherein each instance of ⌇⌇⌇ of Formulae (I) and (II) represents a portion of the collagenous substrate; wherein the $R^1$ is represented by a structure selected from the group consisting of: $-(CH_2)_a-(O-(CH_2)_b)_c-O-(CH_2)_d-$, $-(CH_2)_a-(NH-(CH_2)_b)_c-NH-(CH_2)_d-$, and $-(CH_2)_a-$, where each of a, b, c, and d is independently an integer equal to 0, 1, 2, 3, 4, 5, 6, 7, or 8; wherein $R^1$ is represented by $-CH_2-O-(CH_2)_b-O-CH_2-$ and b is 4; wherein the crosslink is further represented by Formula (Ia):

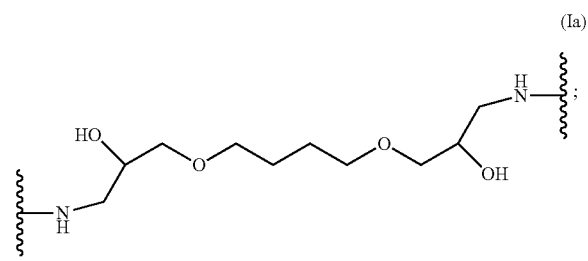

(Ia)

wherein the $R^2$ is represented by a structure selected from the group consisting of: $-(CH_2)_a-(O-(CH_2)_b)_c-O-(CH_2)_d-H$, $-(CH_2)_a-(NH-(CH_2)_b)_c-NH-(CH_2)_d-H$, and $-(CH_2)_a-H$, where each of a, b, c, and d is independently an integer equal to 0, 1, 2, 3, 4, 5, 6, 7, or 8; wherein the quenched crosslinking agent is represented by Formula (IIa):

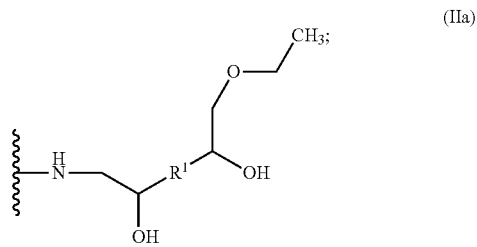

(IIa)

wherein the reinforced collagen matrix device is configured for tendon, ligament, and/or other tissue repair, support, reconstruction and/or other treatment in any distal extremity joint in the body; wherein the reinforced collagen matrix device is configured for tendon, ligament, and/or other tissue repair, support, reconstruction and/or other treatment of a patient's ankle, knee, wrist, hand, or foot.

Also disclosed herein are embodiments of a tissue attachment device that can be used for soft tissue and tendon repair. In any embodiments disclosed herein, the tissue attachment device can include a collagen matrix cover that can have or be made from collagen, and at least one reinforcement strip coupled with the collagen matrix cover. Any embodiments of a reinforced collagen matrix device and/or methods of using any of the embodiments of the reinforced collagen matrix device disclosed herein can include, in additional embodiments, one or more of the following steps, features, components, and/or details, in any combination with any of the other steps, features, components, and/or details of any other embodiments disclosed herein: wherein the reinforcement strip can include a polymeric surgical mesh material; wherein the tissue attachment device can have two reinforcement strips coupled with the collagen matrix cover; wherein the reinforcement strips can be longer than the collagen matrix cover; wherein the tissue attachment device can be configured to cover any joint or sliding tendinous structure; wherein the collagen matrix cover can have a trapezoidal or rectangular shape; wherein the collagen matrix cover can have an ovoidal shape; wherein the collagen matrix cover can have a triangular shape; and/or wherein the collagen matrix cover can be configured to be cut in an anatomical shape to match a shape of a natural tendinous structure requiring surgical repair.

Also disclosed herein are embodiments of a reinforced collagen matrix for soft tissue and tendon repair incorporating collagen reinforced with a polymeric surgical mesh material. Some embodiments of the reinforced collagen matrix can be configured to cover any exposed polymeric mesh material in a joint or sliding tendinous structure. In some embodiments, the reinforced collagen matrix can be in the shape of a trapezoid or rectangle, or have an ovoid or triangular shape. In some embodiments, the reinforced collagen matrix can be cut in an anatomical shape to match a natural tendinous structure requiring surgical repair.

DETAILED DESCRIPTION OF SOME EXEMPLIFYING EMBODIMENTS

Disclosed herein are embodiments of orthopedic devices comprising collagen-based materials. The term "orthopedic," as it is used herein, is meant to refer to devices that are configured to treat or are related to the treatment of deformities of bones, muscles, ligaments, tendons, and/or other connective tissue. The term "soft tissue," as used herein, is meant to refer to tissues that connect, support, or surround other structures and organs of the body. Nonlimiting examples of soft tissue include muscles, tendons, ligaments, fascia, nerves, fibrous tissues, fat, blood vessels, and synovial membranes, any or all of which are meant to be included in any use of the term soft tissue herein.

Figure 1:
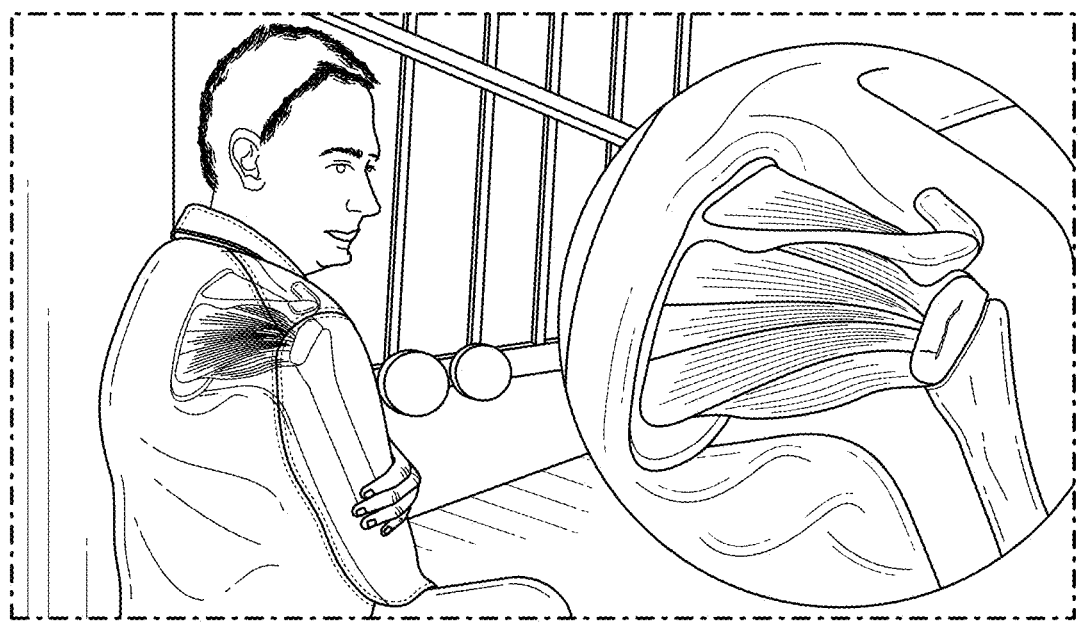
FIG. 1 depicts the anatomical location of a rotator cuff tear.
Figure 2:
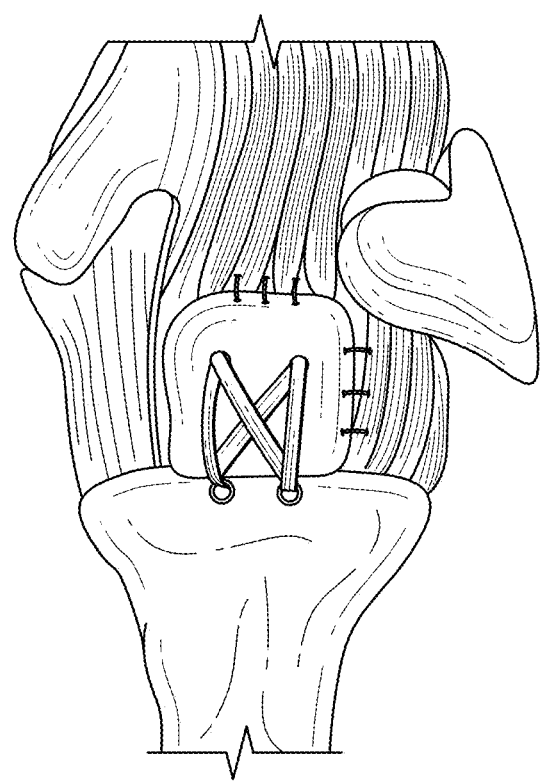
FIG. 2 illustrates a front view of an example of a conventional endoscopic superior capsule repair (SCR) method.
Figure 3:
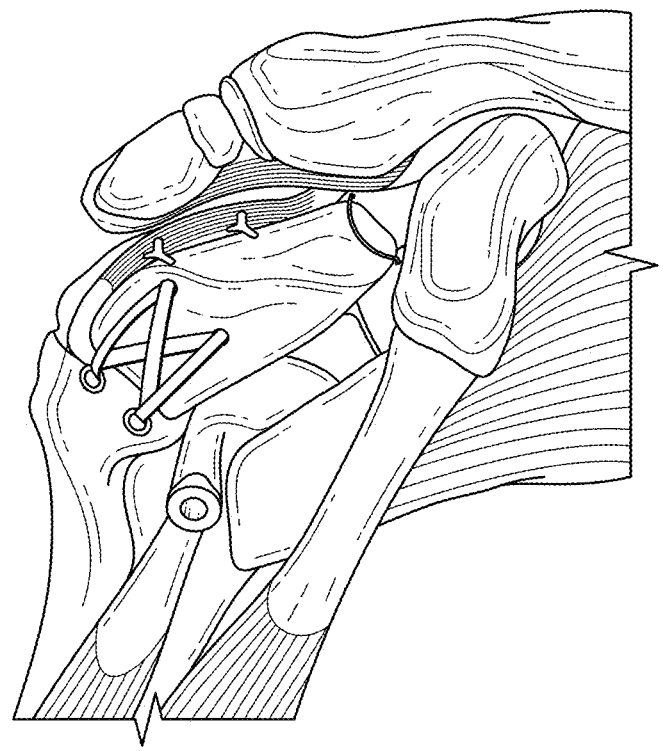
FIG. 3 illustrates a side view of the example of the conventional endoscopic SCR method shown in FIG. 2.
Figure 4:
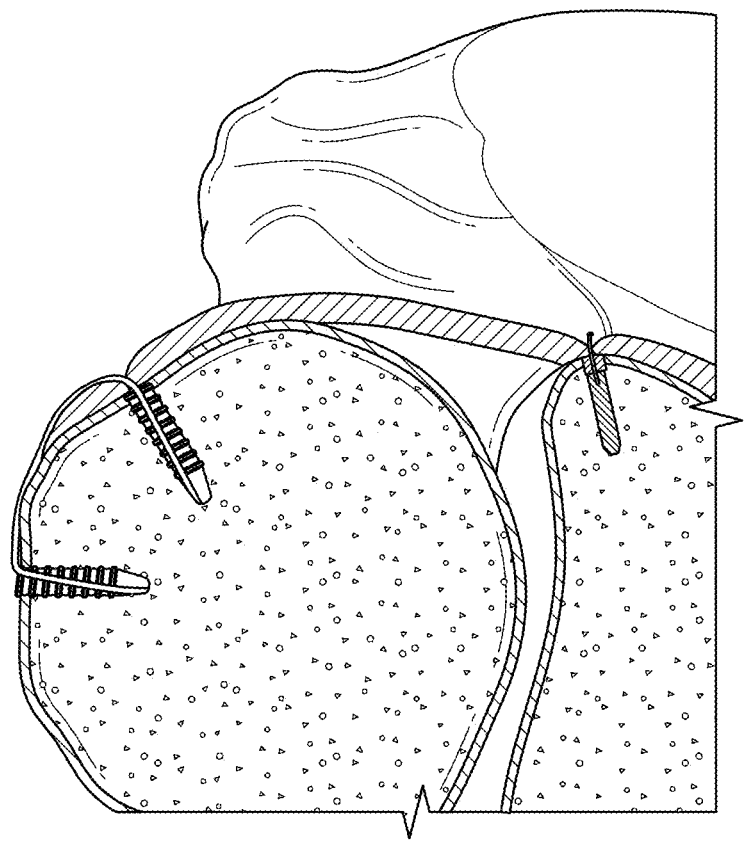
FIG. 4 illustrates a section view of the example of the conventional endoscopic SCR method shown in FIG. 2.
Figure 5:
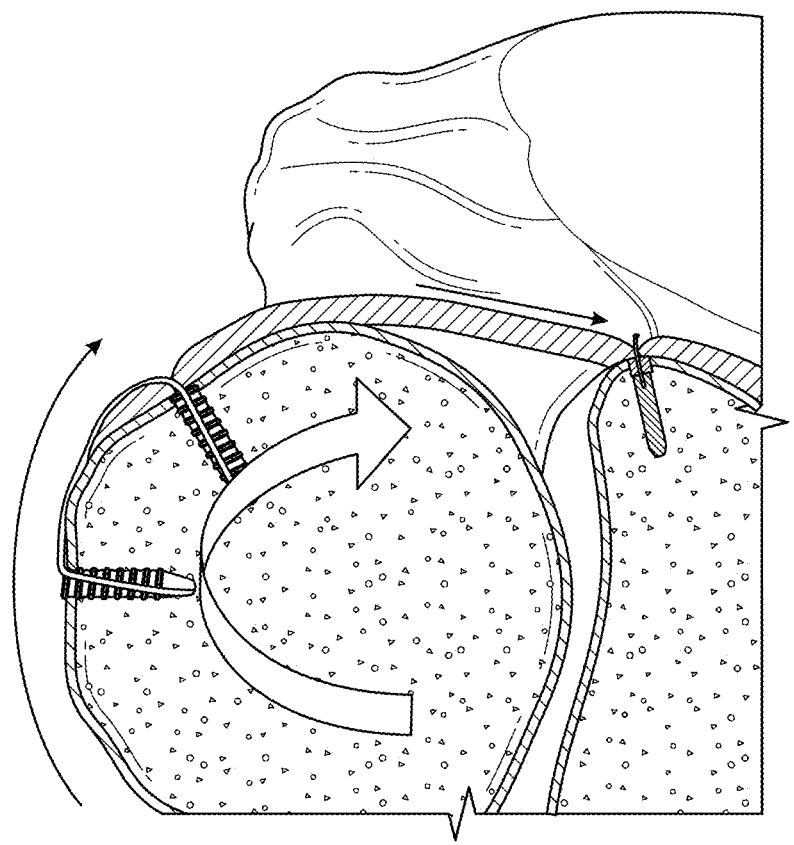
FIG. 5 illustrates a section view of an example of a conventional endoscopic SCR method under high loading and torsion at the suture sites.

FIG. 1 illustrates an example of a rotator cuff tear and the anatomical location of the rotator cuff. FIG. 2 illustrates a front view of an example of a conventional method of endoscopic superior capsule repair (SCR). FIGS. 3 and 4 illustrate a side view and a cutaway view, respectively, of the example of the conventional endoscopic SCR method shown in FIG. 2. FIG. 5 illustrates high loading and torsion at the suture sites of the conventional method of endoscopic SCR illustrated in FIG. 2. Conventional endoscopic SCR methods and devices can result in weak suture to collagen attachments. In some conventional SCR methods and devices, the sutures can cut through the collagen, can rupture or break, or can fail in other ways.

Figure 11:
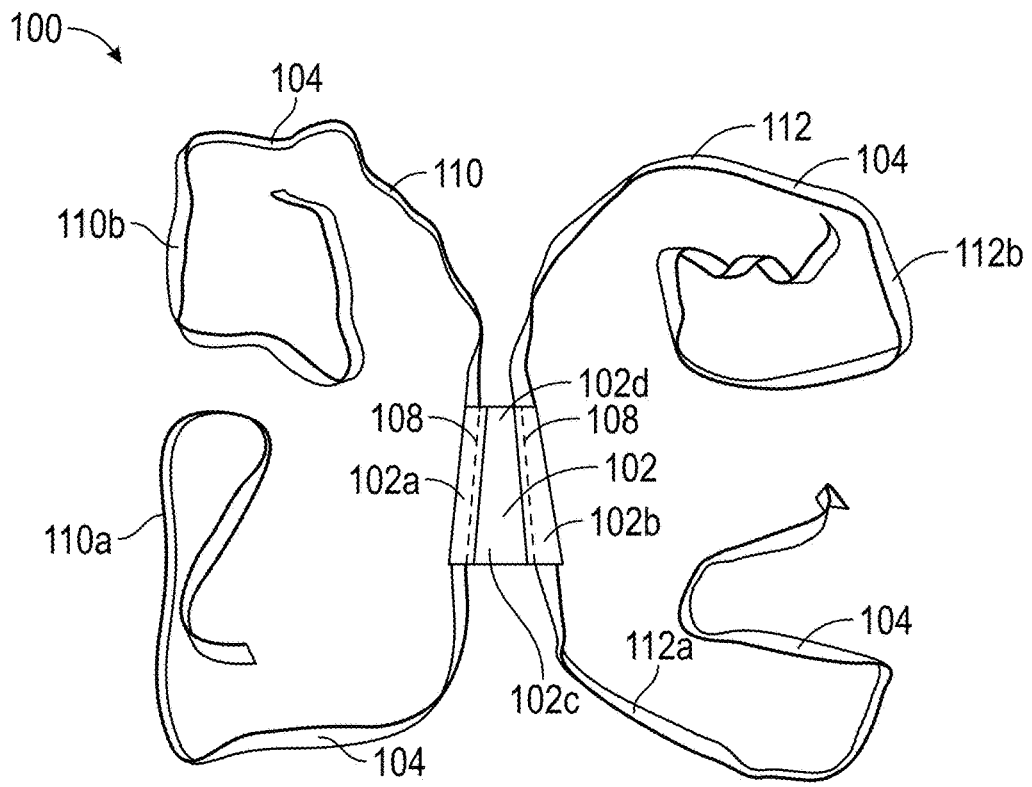
FIG. 11 illustrates another embodiment of an SCR device.

The embodiments of the reinforced collagen matrix device 100 (also referred to as a tissue matrix apparatus) for arthroscopic surgical repair of tendinous and other soft tissue disclosed herein can provide a more robust solution for SCR and provide greater therapeutic benefits to patients undergoing SCR procedures. For reference, reinforced collagen matrix devices 100 may also be referred as orthopedic implants herein. FIG. 11 shows an embodiment of reinforced collagen matrix device 100 that can be used for endoscopic SCR procedures. In some embodiments, the reinforced collagen matrix devices 100 can have a collagen matrix cover 102 (also referred to herein as a matrix layer) of any desired shape, including a trapezoidal shape as shown. The collagen matrix cover 102 may also be referred to herein as a crosslinked collagen-based material. One or more reinforcement strips 104 can be coupled with the collagen matrix cover 102 using any suitable methods, including using stitches 108 that can include sutures 109, using adhesive, staples, and/or other fasteners or fastening means. For example and without limitation, in some embodiments, the reinforced collagen matrix devices 100 can have two continuous reinforcement strips 104 coupled with the collagen matrix cover 102 such that the ends of the reinforcement strips 104 extend beyond the collagen matrix cover 102. For example, a first reinforcement strip 110 can be coupled with a first side portion 102a of the collagen matrix cover 102 and a second reinforcement strip 112 can be coupled with a second side portion 102b of the collagen matrix cover 102. The first and second reinforcement strips 110, 112 can coupled with the collagen matrix cover 102 using one or more stitches 108 comprising sutures, using adhesive, staples, and/or other fasteners or fastening means. For example, in some embodiments, the first reinforcement strip 110 can be coupled with the first side portion 102a of the collagen matrix cover 102 such that a first end 110a of the first reinforcement strip 110 extends beyond a first end 102c of the collagen matrix cover 102 and such that a second end 110b of first reinforcement strip 110 extends beyond a second end 102d of the collagen matrix cover 102. In some embodiments, the second reinforcement strip 112 can be coupled with the second side portion 102b of the collagen matrix cover 102 such that a first end 112a of the second reinforcement strip 112 extends beyond a first end 102c of the collagen matrix cover 102 and such that a second end 112b of the second reinforcement strip 112 extends beyond a second end 102d of the collagen matrix cover 102. The first ends 110a, 112a and the seconds ends 110b, 112b of the first and second reinforcement strips 110, 112 can be used to advance the reinforced collagen matrix devices 100 through a port to the desired anatomical position and to secure the reinforced collagen matrix devices 100 in the desired anatomical position. The first and second reinforcement strips 110, 112 can have a long length and can be trimmed before and/or after placement of the reinforced collagen matrix devices 100.

Matrix Cover

Figure 6:
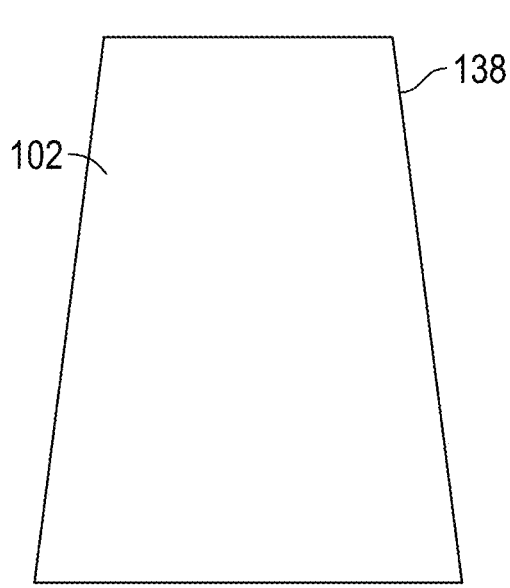
FIG. 6 illustrates an embodiment of a collagen matrix.
Figure 18:
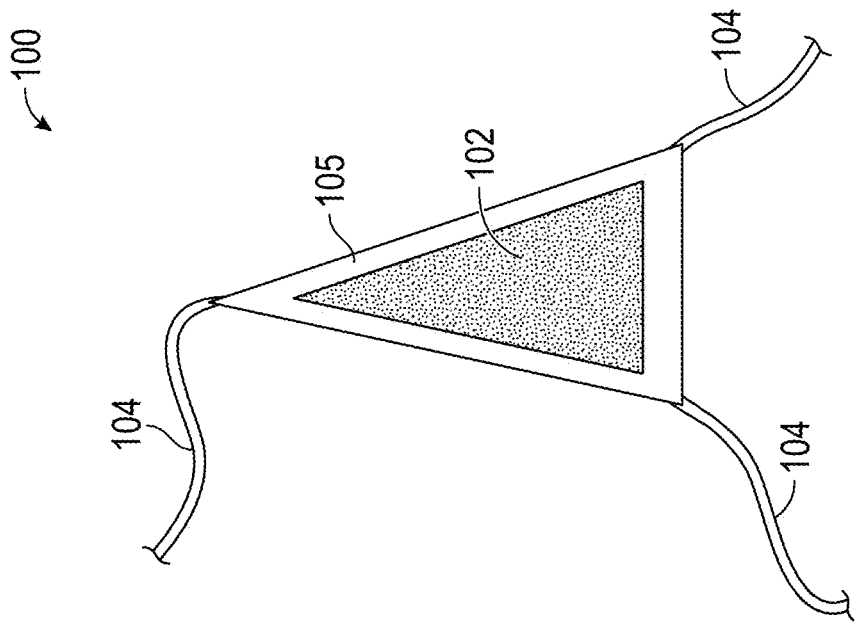
FIG. 18 illustrates another embodiment of an SCR device.
Figure 17:
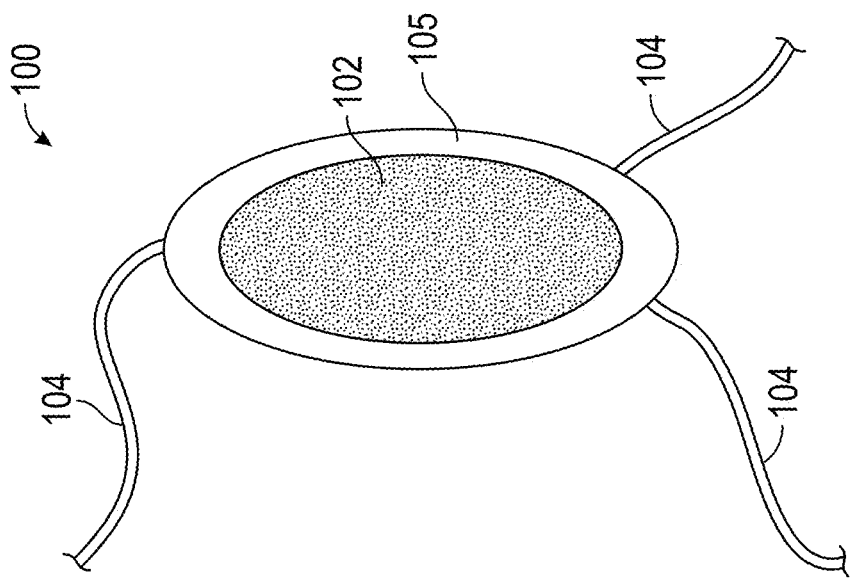
FIG. 17 illustrates another embodiment of an SCR device.

FIG. 6 illustrates an embodiment of a collagen matrix cover 102 that can be used in any of the embodiments of the reinforced collagen matrix devices 100 disclosed herein. In any embodiments disclosed herein, the collagen matrix cover 102 can have a trapezoidal shape as shown in FIG. 6a, a rectangular shape, a circular shape, an ovoid shape as shown in FIG. 17, a triangular shape as shown in FIG. 18, or any other desire shape.

Figure 7:
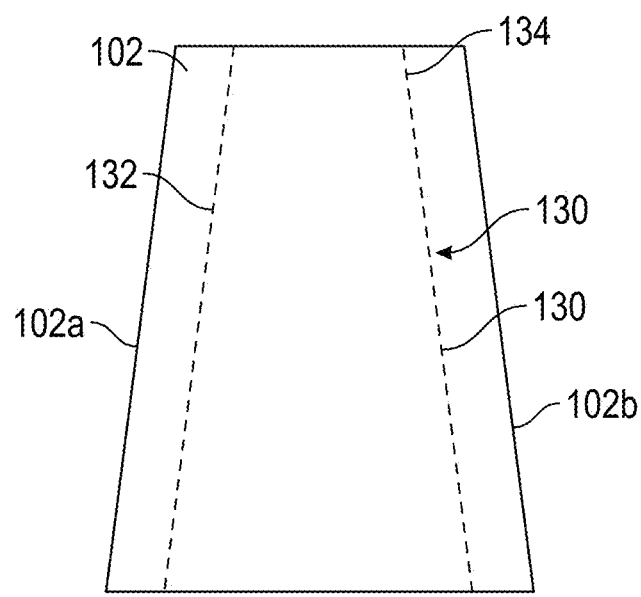
FIG. 7 illustrates the embodiment of the collagen matrix shown in FIG. 6, showing biasing lines used for manufacturing an SCR device.

In some embodiments, with reference to FIG. 7, the collagen matrix cover 102 can have one or more biasing lines 130 along a portion of the collagen matrix cover 102. The biasing lines 130 can be or include perforations, score line(s), cut lines, partial cut lines, lines of reduced cross-sectional thickness, or lines or portions of the collagen matrix cover 102 that are otherwise biased to cause the collagen matrix cover 102 to fold therealong. In some embodiments, the collagen matrix cover 102 can be folded over along the one or more biasing lines 130. With reference to FIG. 7, the collagen matrix cover 102 can have a first biasing line 132 generally parallel with the first side 102a of the collagen matrix cover 102 and a second biasing line 134 generally parallel with the second side 102b of the collagen matrix cover 102 such that the collagen matrix cover 102 can be folded along the first and second biasing lines 132, 134.

For example and without limitation, the collagen matrix cover 102 (any embodiments of which can be fully or partially crosslinked, but is not required to be) can include a sheet 138 of the collagenous material (also referred to herein as a collagenous substrate) that can be wrapped around at least a first main surface, a second main surface, and the first side edge surface of a portion of the one or more reinforcement strips 104. Any embodiments of the collagen matrix cover 102 can include a sheet 138 of the collagenous material that can be wrapped continuously around the first main surface, the second main surface, the first side edge surface, and the second side edge surface of the one or more reinforcement strips 104.

Some embodiments of the collagen matrix cover 102 or the sheet 138 thereof can have at least one biasing line along a length thereof, as described above. The biasing line 130 can be configured to facilitate the wrapping and/or bending of the sheet 138 of the collagenous material on itself (in embodiments where there is no additional layer or reinforcing material), and/or to facilitate the wrapping and/or bending of the sheet 138 of the collagenous material over and/or around one or more reinforcement strips 104. One or more folds or biasing lines 130 can be positioned in a middle portion of the sheet 138, along a centerline of the sheet 138, adjacent to the middle portion of the sheet 138, or at any desired position or location on the sheet 138.

Some embodiments of the sheet 138 or other collagen matrix cover 102 can include two or more folds or biasing lines 130, for example and without limitation, two or more folds or biasing lines 130 can extend along a length of the sheet 138 and be oriented to align with the first side edge 102*a* and the second side edge 102*b* of the collagen matrix cover 102 so that the sheet 138 can be wrapped around the one or more reinforcement strips 104 and cover the first side edge surface and the second side edge surface and the main surfaces of the reinforcement strips 104. In some embodiments, the one or more biasing lines 130 can facilitate a more uniform height or thickness of the collagen matrix cover 102 along a length and over a width of the collagen matrix cover 102 and/or of the SCR device 100 along the middle portion of the one or more reinforcement strips 104 or other portion of the reinforced collagen matrix device 100 covered by the collagen matrix cover 102.

In some embodiments, the collagen matrix cover 102 and/or sheet 138 of collagen matrix cover 102 can include one or more cuts along a length thereof. In some embodiments, the one or more cuts can coincide with one or more folds or biasing lines 130 formed in the sheet 138 to further facilitate wrapping of the collagen matrix cover 102 around and/or over the one or more reinforcement strips 104, or to further facilitate the folding of the sheet 138 or the collagen matrix cover 102 on itself in embodiments that do not have the one or more reinforcement strips 104.

In some embodiments, the at least one fold or biasing line 130 can be aligned with the first side edge surface of the one or more reinforcement strips 104. In some embodiments, the one or more cuts can include or can form at least one channel having a reduced thickness along the at least one channel. The reduced thickness can be less than a thickness of the collagen matrix cover 102 adjacent to the at least one channel. In some embodiments, the reduced thickness of the channel can be approximately 0.1 mm, and the thickness of the collagen matrix cover 102 adjacent to the at least one channel can be approximately 0.5 mm. In some embodiments, the reduced thickness of the channel can be from 10% to 50% of the thickness of the collagen matrix cover 102 adjacent to the at least one channel, or from 15% to 30% of the thickness of the collagen matrix cover 102 adjacent to the at least one channel, or approximately 20% of the thickness of the collagen matrix cover 102 adjacent to the at least one channel.

Figure 8:
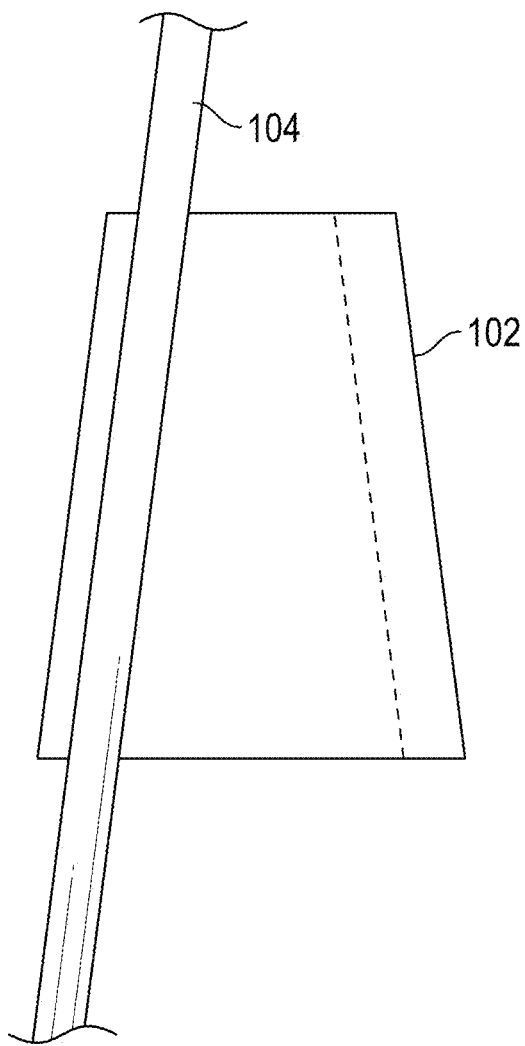
FIG. 8 illustrates another optional step in an embodiment of an assembly process of an SCR device, wherein a first reinforcement strip is being assembled with the collagen matrix.
Figure 9:
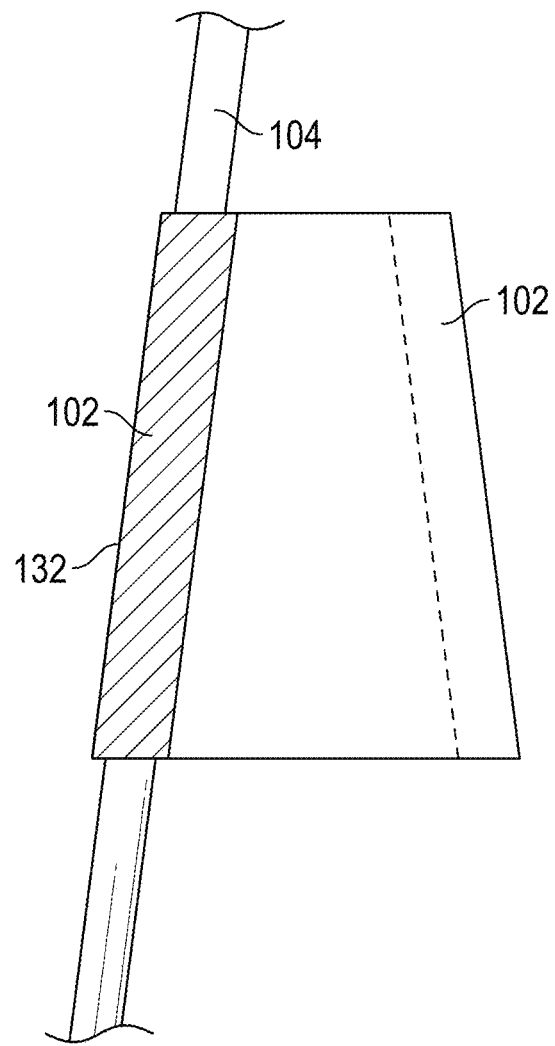
FIG. 9 illustrates another optional step in an embodiment of an assembly process of an SCR device, wherein a portion of the collagen matrix is being folded over the first reinforcement strip.
Figure 10:
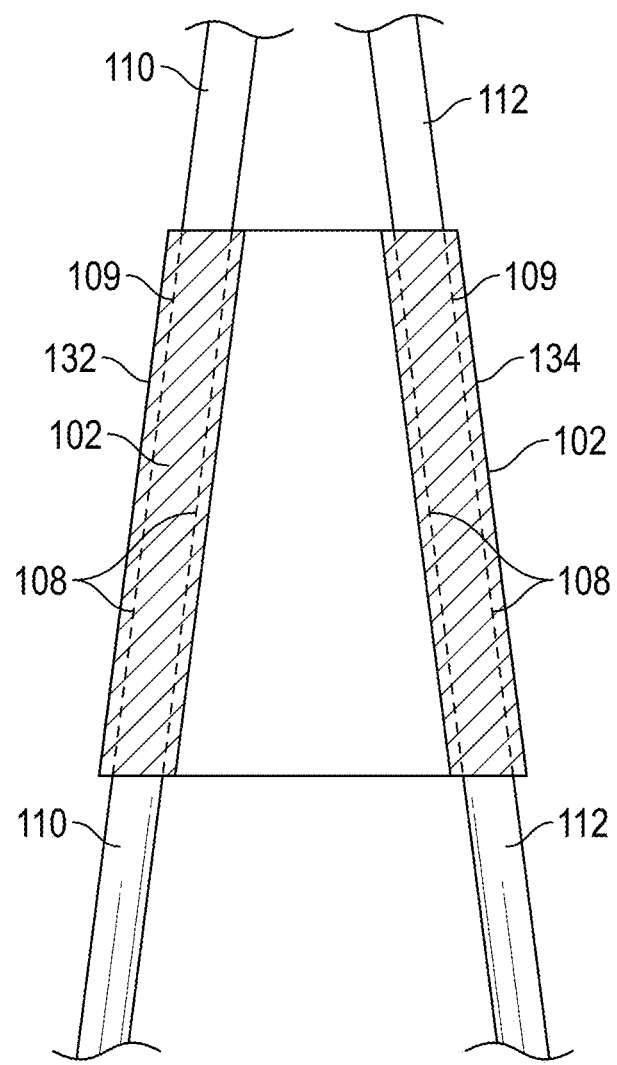
FIG. 10 illustrates another optional step in an embodiment of an assembly process of an SCR device, wherein a portion of the collagen matrix is being folded over the first reinforcement strip.

The crosslinked collagen-based material of the collagen matrix cover 102 can be folded and sewn to cover and to couple with at least a portion of the one or more reinforcement strips 104 that are coupled with the collagen matrix cover 102, as shown in FIGS. 8-10. The collagen matrix cover 102 can be positioned over the portion of the reinforcement strips 104 so as to completely cover and surround the portion of the reinforcement strip 104 along the length of the collagen matrix cover 102.

Again, in any embodiments disclosed herein, the collagen matrix cover 102 or other components of the device can be generally trapezoidal, triangular, circular, ovoid, polygonal, or of any other desired shape, depending on the anatomical requirements of the surgical repair location or at the discretion or desire of the surgeon. For example, any embodiments of the collagen matrix cover 102 disclosed herein can be formed so that, in an assembled state, the collagen matrix cover 102 has a trapezoidal shape as shown in FIG. 10 or FIG. 19.

Figure 19:
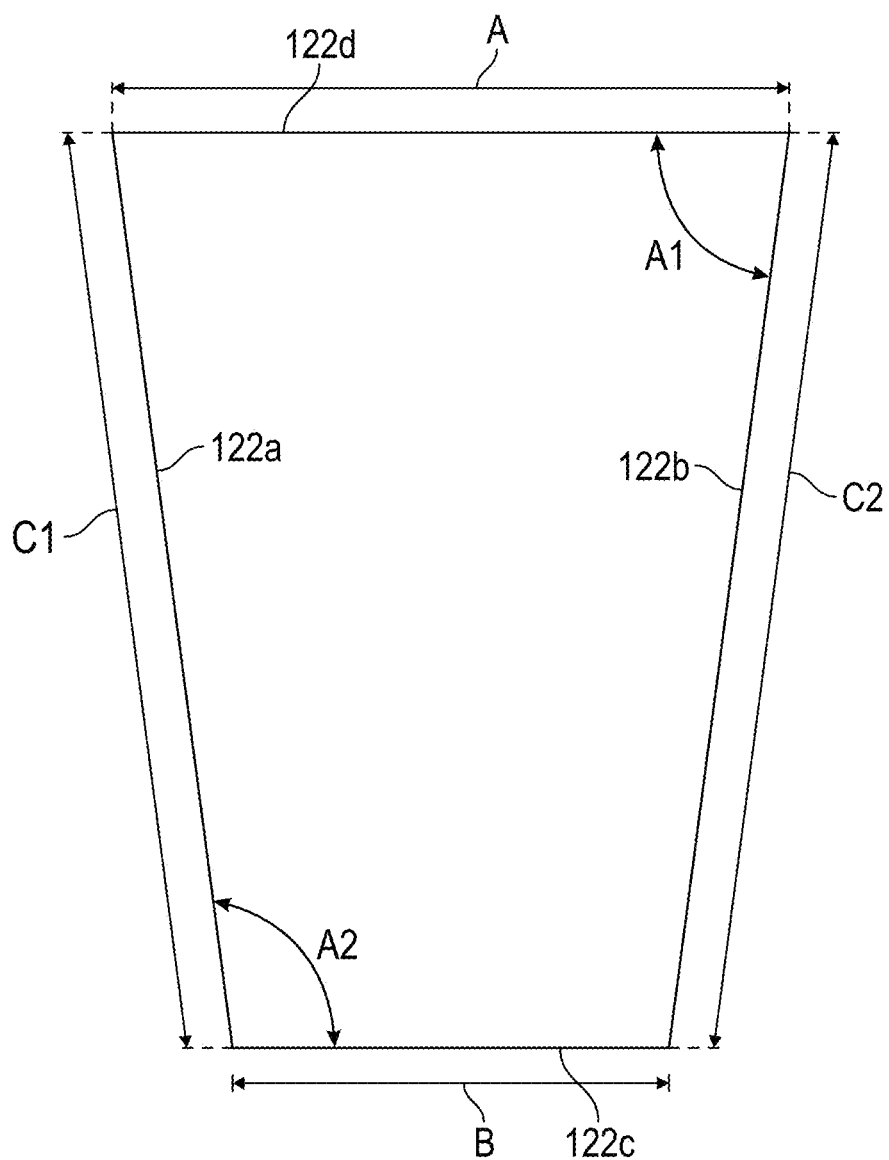
FIG. 19 illustrates some exemplifying dimensions of an embodiment of an SCR device.

With reference to FIG. 19, in some embodiments, the collagen matrix cover 102 can have a first end edge 102*c* having a first side edge 122*a* having a length C1, a second side edge 122*b* having a length C2, a first end edge 122*c* having a length B, and a second end edge 122*d* having a length A. In any embodiments disclosed herein, the length C1 of the first side edge 122*a* can be the same or approximately the same as the length C2 of the second side edge 122*b*. The side edges can be the edges that the reinforcement strips extend along or adjacent to.

To provide an optimal anatomical fit for SCR, in any embodiments disclosed herein, the length A of the second end edge 122*d* in an assembled state can be greater than the length B of the first end edge 122*c*. For example and without limitation, the length A of the second end edge 122*d* in an assembled state can be 1.6 times greater than the length B of the first end edge 122*c*, or approximately (for example, within ±10%) 1.6 times greater than the length B of the first end edge 122*c*. Further, in any embodiments, the length C1 and/or C2 of the first and/or second side edge 122*a*, 122*b* in an assembled state can be 1.6 times greater than the length A of second end edge 122*d*, or approximately (for example, within ±10%) 1.6 times greater than the length A of second end edge 122*d*. The overall size of the assembled matrix apparatus can change depending on the size of the patient's anatomy. However, in some embodiments, the ratios listed above and the angles listed below can be maintained.

Further, any embodiments of the collagen matrix cover disclosed herein can be formed so that, in an assembled state, the collagen matrix cover defines an angle A1 between the second end edge 122*d* (having length A) and the first or second side edge (having length C1 or C2, respectively) and an angle A2 between the first side edge (having length C1) or the second side edge (having length C2) and the first end edge 122*c* (having length B). In some embodiments, the angle A1 can be 82.5 degrees, or approximately 82.5 degrees (e.g., 82.5 degrees ±2.5 degrees) and the angle A2 can be 96.5 degrees, or approximately 96.5 degrees (e.g., 96.5 degrees±2.5 degrees).

With reference to FIG. 17, any embodiments of the reinforced collagen matrix devices 100 disclosed herein can have a collagen matrix cover 102 having a generally curved, circular, or ovoid shape (as shown in FIG. 17). The reinforced collagen matrix devices 100 can have a plurality of reinforcement strips 104 coupled with the collagen matrix cover 102 and/or coupled with a peripheral reinforcement 105 that can surround a periphery of the collagen matrix cover 102. The peripheral reinforcement 105 can have a shape that generally matches the shape of the collagen matrix cover 102. As shown, the reinforced collagen matrix devices 100 of FIG. 17 can have three reinforcement strips 104 coupled with the collagen matrix cover 102 and/or the peripheral reinforcement 105, wherein one reinforcement strip 104 extends from a first end portion of the collagen matrix cover 102 and two reinforcement strips 104 from a second end portion of the collagen matrix cover 102.

With reference to FIG. 18, any embodiments of the reinforced collagen matrix devices 100 disclosed herein can have a collagen matrix cover 102 having a generally triangular shape. the reinforced collagen matrix devices 100 can have a plurality of reinforcement strips 104 coupled with the collagen matrix cover 102 and/or coupled with a peripheral reinforcement 105 that can surround a periphery of the collagen matrix cover 102. The peripheral reinforcement 105 can have a shape that generally matches the shape of the collagen matrix cover 102. As shown, the reinforced collagen matrix devices 100 of FIG. 18 can have three reinforcement strips 104 coupled with the collagen matrix cover 102 and/or the peripheral reinforcement 105, wherein one reinforcement strip 104 extends from a first end portion of the collagen matrix cover 102 and two reinforcement strips 104 from a second end portion of the collagen matrix cover 102. The reinforcement strips 104 can each extend generally from the corners of the triangular collagen matrix cover 102 or the peripheral reinforcement 105.

Reinforcement Strips

In any embodiments disclosed herein, the reinforcement strips 104 can be made from a mesh medical tape or, in other embodiments, from one or more strands or sutures of a biocompatible polymeric material or other suitable material that are braided. For example and without limitation, some embodiments of the reinforcement strips can include braided sutures made from polyethylene and/or ultra-high molecular weight polyethylene (UHMWPE), polyetheretherketone (PEEK), and/or any other suitable or desired materials. The reinforcement strips of any embodiments disclosed herein can include one or more sutures made from a multi-stranded, long chain UHMWPE core with a braided jacket of polyester and UHMWPE. In any embodiments disclosed herein, the reinforcement strips can be made from a sheet of material, such as polytetrafluoroethylene (PTFE) or other suitable or desired material. The sheet of material can be die cut to the desired shape of the reinforcement strips, or otherwise formed to the desired shape of the reinforcement strips.

The reinforcement strips 104, which can be made from a polymeric biocompatible material, can be made of any suitable polymeric materials in a mesh, woven, fabric, knitted or solid form, for example and without limitation. The material can be biocompatible and have a tensile strength designed to accommodate the loads and stresses that are typically experienced in a shoulder, abdominal, ankle, hip or other anatomical soft tissue repairs. In any embodiments, the reinforcement strip can comprise a suture or a plurality of sutures grouped together, grouped together in parallel strands, woven together, braided, and/or otherwise bound together.

In any embodiments disclosed herein, the reinforcement strips 104 can include at least one of a thread, a suture, a sheet, a strip, a fabric, a mesh material such as a polymeric surgical mesh material, a weave, and any combination of the foregoing. In some embodiments, the reinforcement strips 104 can include a woven material that can vary along a length thereof—e.g., can be wider in the middle portion of the reinforcement strip 104 than in the end portions of the reinforcement strips 104. For example and without limitation, in some embodiments, the first width of the middle portion of the reinforcement strips 104 can be greater than a width of the first end portion and/or the second end portion of the reinforcement strips 104.

Figure 12:
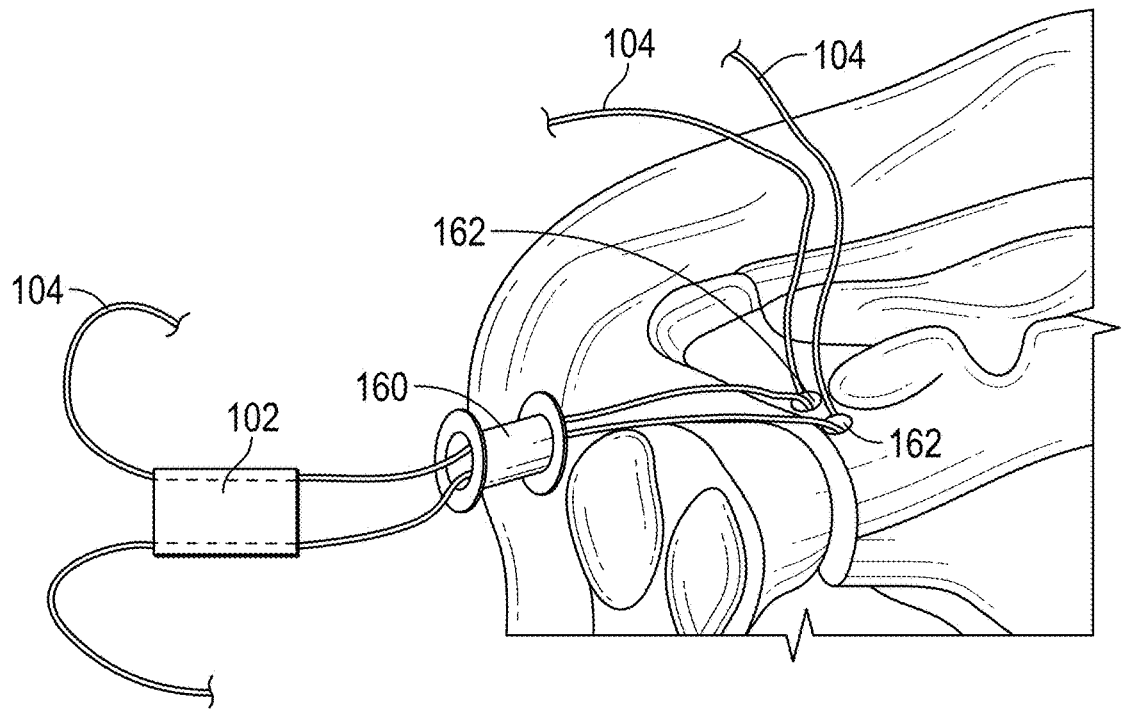
FIG. 12 illustrates a portion of an exemplifying arthroscopic surgical method of implanting an embodiment of the SCR device.
Figure 13:
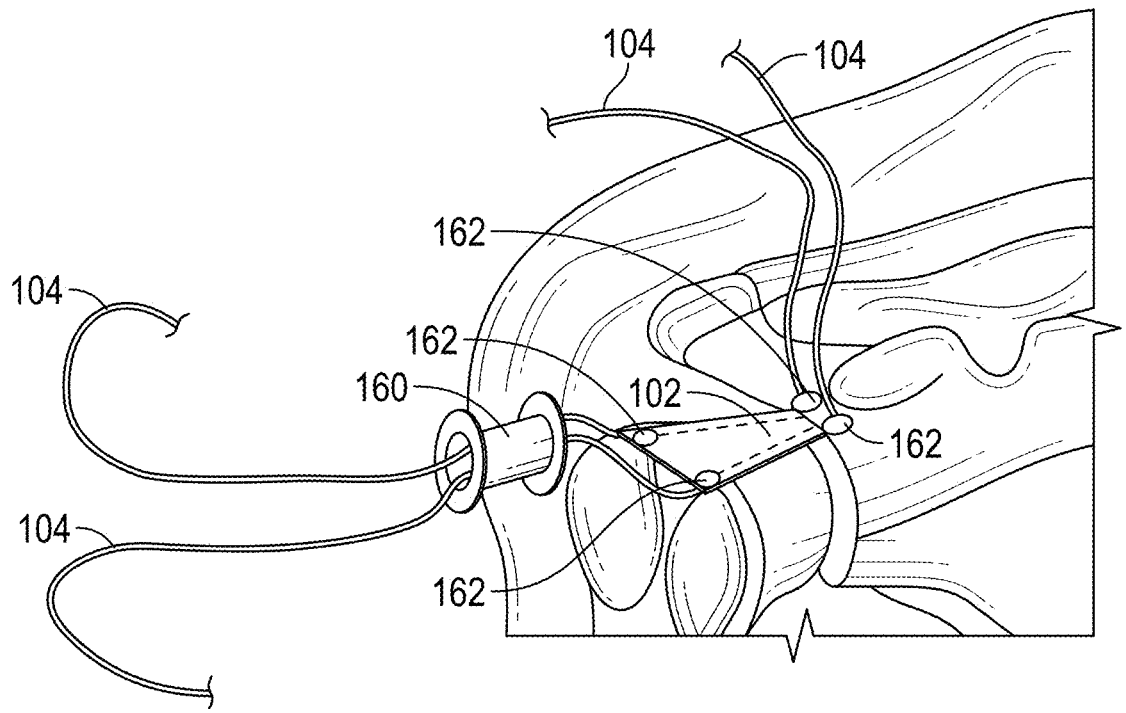
FIG. 13 illustrates an additional portion of an exemplifying arthroscopic surgical method of implanting the SCR device shown in FIG. 12.
Figure 14:
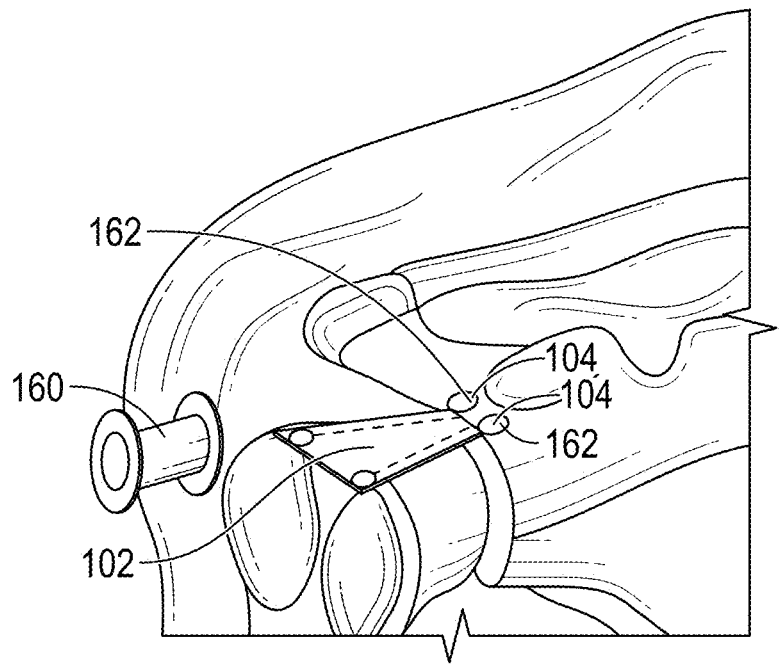
FIG. 14 illustrates an additional portion of an exemplifying arthroscopic surgical method of implanting the SCR device shown in FIG. 12.

The long surgical mesh tails (i.e., the ends of the reinforcement strips 104 that extend away from the collagen-matrix cover 102) can be used for precise location for anchoring in an arthroscopic surgical field, as shown in FIGS. 12-14, and can be cut or trimmed after the device has been suitably positioned or anchored. In some embodiments, the reinforcement strip 104 can have a length L1 from an end of the first end portion to an end of the second end portion of the reinforcement strip 104, and the collagen matrix cover 102 can have a length L2 parallel to the first side edge surface 102a and the second side edge surface 102b. In some embodiments, the length L1 of the reinforcement strip 104 can be greater than the length L2 of the crosslinked collagen-matrix cover 102. In some embodiments, the length L1 of each reinforcement strip 104 can be 1000% greater than (i.e., ten times) the length L2 of the collagen matrix cover 102, or can be 1500% greater than (i.e., fifteen times greater) than the length L2 of the crosslinked collagen-based covering 104, or can be from 200% (or approximately 200%) greater than the length L2 of the collagen matrix cover 102 to 1500% (or approximately 1500%, or more than 1500%) greater than the length L2 of the collagen matrix cover 102, or of any value within this range, or from and to any values within this range.

In some embodiments, the assembly/construction process of the device can be configured to minimize the exposure to the underlying reinforcement strips 104 in any joint or areas of moving or sliding surfaces post repair. Patients can experience significant inflammation, irritation, pain, and/or discomfort with even minimal exposure to fabric and/or non-biological materials. Therefore, some embodiments of the reinforced collagen matrix devices 100 disclosed herein can eliminate a traditional cause of inflammation and other negative side effects of exposure to the reinforcement strips in the joint by completely or substantially completely covering the portion of the reinforcement strips that extend over or adjacent to the collagen matrix cover, and can reduce the likelihood cutting through tissue in the affected area, as some sutures of conventional devices do.

In any embodiments disclosed herein, the reinforced collagen matrix device 100 can be configured such that the collagen matrix cover 102 completely covers all surfaces of the reinforcement strips 104 that extend over a length of the collagen matrix cover 102 (for example, all surfaces of the reinforcement strips except that portions of the reinforcement strips that extend past the collagen matrix cover 102). For example and without limitation, some embodiments of the reinforced collagen matrix device can have a collagen matrix cover 102 that extends over a first side of the reinforcing mesh strip, is folded over, and returns back so as to extend over the outer edge or side of the reinforcing strip and at least a second side of the reinforcing strip 104, wherein the second side of the reinforcement strips is opposite to the first side of the reinforcement strip. In this configuration, having the collagen matrix cover 102 extend continuously over the first side, outer edge or side, and at least second side of the reinforcement strip prevents exposure of the outer edge of the reinforcing strip 104 from the anatomy surrounding or adjacent to the reinforced collagen matrix device 100, which can reduce or eliminate inflammation, irritation, pain, and/or discomfort to the tissue that surrounds or is adjacent to the reinforcement strips 104, particularly the outer edge of the reinforcement strips 104.

Additionally, some embodiments of the reinforced collagen matrix device 100 can have a collagen matrix cover 102 that extends over a first side of the reinforcement strip, is folded over, and returns back so as to extend over the outer edge or side of the reinforcing mesh strip, at least a second side of the reinforcement strip, and an inner edge or side of the reinforcement strip so as to completely cover the portion of the reinforcement strip (or strips, if more than one) that extend over or adjacent to the collagen matrix cover 102. For example and without limitation, the inner edge or side of the reinforcement strip can be covered by the collagen matrix cover 102 and, in some embodiments, one or more stitches can extend along a length of the collagen matrix cover 102 that can essentially seal off or partially seal off the return edge of the collagen matrix cover 102 and the inner edge of the reinforcement strip that is covered by the collagen matrix cover 102.

For example, in some embodiments, sutures can be sewn through one or both layers of the collagen matrix cover 102 (i.e., both layers of the collagen matrix cover 102 that have been folded over the reinforcement strip) and the reinforcement strip (e.g., surgical mesh tape) on each side of the collagen matrix cover 102 to secure the reinforcement strip to each side of the collagen matrix cover 102. In this configuration, the reinforcement strips can be secured to the collagen matrix cover 102 in an axial direction of the reinforcement strips also to prevent, for example and without limitation, the reinforcement strips from sliding relative to the collagen matrix cover 102. One or two, or more, rows of sutures can pass through the reinforcement strip and collagen matrix cover 102 to secure the reinforcement strips to each side of the collagen matrix cover 102. The sutures can be arranged in a linear pattern, a zig-zag pattern, or in any other suitable pattern. In other embodiments, one or more sutures can be positioned along one or both sides of the reinforcement strip and pass through both layers of the collagen matrix cover 102 without passing through the reinforcement strips. In some embodiments, this can be done to allow the reinforcement strips to be slideable relative to the collagen matrix cover 102.

Stitching

In any embodiments, the collagen matrix cover 102 can be attached to the one or more reinforcement strips 104 with stitching 108 that can include sutures 109 or other suitable stitching material. The stitching 108 can pass through the collagen matrix cover 102 or can be configured to pass only through the reinforcement strips 104. The stitching 108 in any embodiments can pass through the one or more reinforcement strips 104 and/or the collagen matrix cover 102. For example, the stitching 108 can pass through both layers of the collagen matrix cover 102 and each of the one or more reinforcement strips 104. Some embodiments of the reinforced collagen matrix device 100 can have multiple lines of stitching 108 extending along a length of the collagen matrix cover 102.

In some embodiments, the stitching 108 can extend through one or both layers of the collagen matrix cover 102 (i.e., both layers of the collagen matrix cover 102 that have been folded over the one or more reinforcement strips 104) and the reinforcement strip 104 that is on the first side 102*a* and the second side 102*b* of the collagen matrix cover 102 to secure the one or more reinforcement strips 104 to each side of the collagen matrix cover 102. In this configuration, the one or more reinforcement strips 104 can be secured to the collagen matrix cover 102 in an axial direction of the one or more reinforcement strips 104 also to prevent, for example and without limitation, the one or more reinforcement strips 104 from sliding relative to the collagen matrix cover 102. Stitching comprising one or two, or more, rows of sutures can pass through the one or more reinforcement strips 104 and collagen matrix cover 102 to secure the one or more reinforcement strips 104 to each side of the collagen matrix cover 102.

Figure 16:
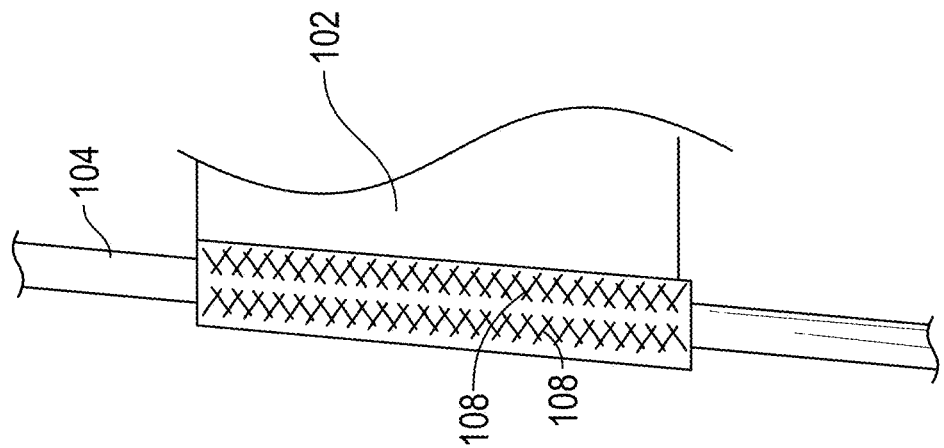
FIG. 16 illustrates another embodiment of an SCR device.
Figure 15:
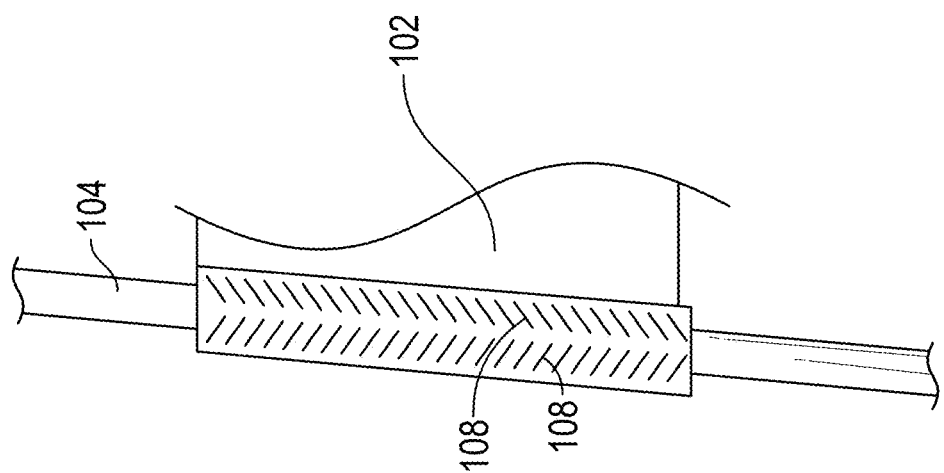
FIG. 15 illustrates another embodiment of an SCR device.

The sutures can be arranged in a linear pattern, a zig-zag pattern, or in any other suitable pattern. In some embodiments, a baseball stitching pattern, a herringbone stitching pattern, or other suitable stitching pattern (for example, as shown in FIGS. 15 and 16) can be used to essentially seal off or partially seal off the return edge of the collagen matrix cover and the inner edge of the reinforcement strip that is covered by the collagen matrix cover. Such stitches can have a first portion that engages both matrix layers only and a second portion that engages both matrix layers and the reinforcement strip. The individual stitches can be at an angle that extends over the inner edge or side of the reinforcement strip.

In other embodiments, one or more sutures can be positioned along one or both sides of the one or more reinforcement strips 104 and pass through both layers of the collagen matrix cover 102 without passing through the one or more reinforcement strips 104. In some embodiments, this can be done to allow the one or more reinforcement strips 104 to be slideable relative to the collagen matrix cover 102.

In some embodiments, sutures can be sewn through one or both layers of the collagen matrix cover 102 (i.e., both layers of the collagen matrix cover 102 that have been folded over the one or more reinforcement strips 104) and the one or more reinforcement strips 104 (which can be, without limitation, a surgical mesh tape) on each side of the collagen matrix cover 102 to secure the one or more reinforcement strips 104 to each side of the collagen matrix cover 102. In this configuration, the one or more reinforcement strips 104 can be secured to the collagen matrix cover 102 in an axial direction of the one or more reinforcement strips 104 also to prevent, for example and without limitation, the one or more reinforcement strips 104 from sliding relative to the collagen matrix cover 102. One or two, or more, rows of sutures can pass through the one or more reinforcement strips 104 and collagen matrix cover 102 to secure the one or more reinforcement strips 104 to each side of the collagen matrix cover 102.

The stitching 108 can be arranged in a linear pattern, a zig-zag pattern, or in any other suitable pattern. In other embodiments, stitching 108 can be positioned along one or both sides of the one or more reinforcement strips 104 and pass through both layers of the collagen matrix cover 102 without passing through the one or more reinforcement strips 104. In some embodiments, this can be done to allow the one or more reinforcement strips 104 to be slideable relative to the collagen matrix cover 102.

Methods

FIG. 12 illustrates a portion of an exemplifying arthroscopic surgical process used for implanting an embodiment of the reinforced collagen matrix device 100 disclosed herein. The one or more reinforcement strips 104 can be used for advancing the collagen matrix cover 102 through the port 160 toward the target location and for positioning the collagen matrix cover 102 in the target position. The reinforcement strips 104 can be advanced through the port 160 and pulled through a second port, e.g., a Neviaser port, to advance the collagen matrix cover 102 to the desired position for SCR, as shown in FIG. 13. As also shown in FIG. 13, using the device's reinforcement strips 104, the collagen matrix cover 102 can be positioned and anchored at a reinforced site on the device 100 using one or more anchors 162. FIG. 14 illustrates the collagen matrix cover 102 positioned in the target location, with the reinforcement strips 104 coupled with the anchors 162. After anchoring, the reinforcement strips 104 can be cut or trimmed and removed from the surgical field.

Composition of Collagen Matrix Cover

Some embodiments of the collagen matrix cover 102 can be made from a variety of collagen sources, including without limitation human or animal pericardium, dermis, amnion, fascia, and tendon, to name a few. Tissues typically have a relatively high content of Type I collagen. Any embodiments of the collagen matrix devices disclosed herein can also have an organized matrix of collagen fibrils to provide strength and/or elasticity. Intact collagen fibrils have been shown to induce improved healing in the surgical repairs of soft tissue. The tissue can be cross-linked or left in the raw state. Using a partial crosslinking process can allow for timely incorporation of native tissue post-surgery during the healing phase.

Some embodiments disclosed herein are directed to a method of making an reinforced collagen matrix device including shaping a treated crosslinked collagen-based material to provide at least a portion of a reinforced collagen matrix device or cover for SCR, wherein the treated crosslinked collagen-based material is made by exposing a collagen material to a crosslinking solution comprising a crosslinking agent to provide a crosslinked collagen-based material, and exposing the collagen-based material to a quenching agent to provide the treated crosslinked collagen-based material. Some embodiments disclosed herein are directed to a method of making a reinforced collagen matrix device comprising a treated crosslinked collagen-based material, including providing a reinforced collagen matrix device base structure and attaching the treated crosslinked collagen-based material to the reinforced collagen matrix device base structure. In some embodiments, the treated crosslinked collagen-based material can be prepared by crosslinking a collagen material with a crosslinking agent to provide a precursor crosslinked collagen-based material and by quenching any unreacted reactive groups of the crosslinking agent on or within the collagen material to provide the treated crosslinked collagen-based material.

In several embodiments, a crosslinked collagen-based material is formed (e.g., shaped, cut, etc.) into a covering. In several embodiments, the covering is used fixed, adhered, or placed over one or more reinforcement strips or elements (e.g., one or more sutures or other orthopedic devices), or the covering may be used without fixing, adhering or placing it over another orthopedic implant. In several embodiments, using an orthopedic device comprising a crosslinked collagen-based covering, the device has improved biocompatibility upon implantation. In several embodiments, using an orthopedic device comprising a crosslinked collagen-based covering as disclosed herein helps reduce and/or avoid undesired responses to the orthopedic device once implanted (e.g., cytotoxicity, toxicity, foreign body granuloma, scar tissue formation, capsule formation, etc.). In several embodiments, the crosslinked collagen-based material comprises a collagen substrate that has been crosslinked using an epoxide-based crosslinking agent (e.g., a diepoxide, triepoxide, etc.). In several embodiments, after the crosslinked collagen-based material is prepared (e.g., by subjecting it to crosslinking conditions), the crosslinking agent is quenched. It has been surprisingly found that, by subjecting a crosslinked collagen-based material to a quenching reaction after preparation, improved properties are obtained (e.g., lower toxicity lower cytotoxicity, etc.). The following description provides context and examples, but should not be interpreted to limit the scope of the inventions covered by the claims that follow in this specification or in any other application that claims priority to this specification. No single component or collection of components or steps is essential or indispensable. Any feature, structure, component, material, step, or method that is described and/or illustrated in any embodiment in this specification can be used with or instead of any feature, structure, component, material, step, or method that is described and/or illustrated in any other embodiment in this specification.

Many medical products are composed from human or animal tissue-based materials. Examples of these medical products include, for example, heart valves, vascular grafts, urinary bladder prostheses, tendon prostheses, hernia patches, surgical mesh, and skin substitutes. An illustration of a specific human or animal tissue-based product is the heart valve prosthesis. Heart valve prostheses are typically made from either porcine aortic valves or bovine pericardium. Such valves are typically made by pretreating the tissue with glutaraldehyde or other crosslinking agents and sewing the tissue into a flexible metallic alloy or polymeric stent. These tissue starting materials (which may be from any mammal, including humans) mainly consist of or comprise collagen, which provides the tissues with their needed mechanical strength and flexibility.

Collagen-based materials, including whole tissue, are finding increased use in the manufacture of biomedical devices, such as prosthetic implants. Collagen is a naturally occurring protein featuring good biocompatibility. It is the major structural component of vertebrates, forming extracellular fibers or networks in practically every tissue of the body, including skin, bone, cartilage, and blood vessels. As a natural component of the extracellular matrix, collagen provides a good physiological, isotropic environment that promotes the growth and function of different cell types and facilitates rapid overgrowth of host tissue in medical devices after implantation.

Three main types of collagen-based materials can be identified, based on the differences in the purity and integrity of the collagen fiber bundle network initially present in the material. The first type includes whole tissue including non-collagenous substances or cells. As a result of using whole tissue, the naturally occurring composition and the native strength and structure of the collagen fiber bundle network are preserved. Whole tissue xenografts have been used in construction of heart valve prostheses and in many other biomedical prostheses. However, the presence of soluble proteins, glycoproteins, glycosaminoglycans, and cellular components in such whole tissue xenografts may induce an immunological response of the host organism to the implant. The second type of collagen-based material includes only the collagen matrix without the non-collagenous substances. The naturally occurring structure of the collagen fiber bundle network is thus preserved, but the antigenicity of the material is reduced. The fibrous collagen materials obtained by removing the antigenic non-collagenous substances will generally have suitable mechanical properties. The third type of collagen-based material is purified fibrous collagen. Purified collagen is obtained from whole tissue by first dispersing or solubilizing the whole tissue by either mechanical or enzymatic action. The collagen dispersion or solution is then reconstituted by either air drying, lyophilizing, or precipitating out the collagen. A variety of geometrical shapes like sheets, tubes, sponges or fibers can be obtained from the collagen in this way. The resulting materials, however, do not have the mechanical strength of the naturally occurring fibrous collagen structure.

A major problem in the use of collagen-based materials for implantation, and especially whole tissue xenografts in which the donor and recipient are phylogenetically distant, is that these materials are prone to acute rejection. This is a rapid and violent immunological reaction that leads to the destruction of the xenograft. In order to use collagen-based materials in manufactured medical devices, particularly bio-prosthetic implants, their durability and in vivo performance typically need to be protected from an acute immunological reaction. Crosslinking the collagen-based materials may help suppress the antigenicity of the material in order to prevent the acute rejection reaction. In addition, crosslinking is used to preserve or even improve mechanical properties and to enhance resistance to degradation.

Several chemical crosslinking methods for collagen-based materials are known. These methods involve the reaction of a bifunctional reagent with the amine groups of lysine or hydroxylysine residues on different polypeptide chains or the activation of carboxyl groups of glutamic and aspartic acid residues followed by the reaction with an amine group of another polypeptide chain to give an amide bond. Glutaraldehyde (GA) crosslinking of collagen provides materials with a high degree of crosslinking. Glutaraldehyde is a dialdehyde. The aldehyde is able to chemically interact with amino groups on collagen to form chemical bonds. This crosslinking agent is readily available, inexpensive, and forms aqueous solutions that can effectively crosslink tissue in a relatively short period. Using GA crosslinking, increased resistance to biodegradation and improved mechanical properties of collagen-based materials can be achieved. However, crosslinking of collagen-based materials using GA has shown to have cytotoxic characteristics, both in vitro and in vivo. Also, crosslinking of collagen-based materials using GA tends to result in stiffening of the material and calcification.

Crosslinking can also be accomplished with diisocyanates by bridging of amine groups on two adjacent polypeptide chains. In the first step, reaction of the isocyanate group with a (hydroxy)lysine amine group occurs, resulting in the formation of a urea bond. Thereafter a crosslink is formed by reaction of the second isocyanate group with another amine group. Diisocyanates do not show condensation reactions as observed in GA crosslinking. Also, no residual reagents are left in the material. A disadvantage, however, is the toxicity of diisocyanates and limited water solubility of most diisocyanates.

Yet another crosslinking method uses epoxy compounds to crosslink collagen. Epoxy compounds (i.e., epoxides) can undergo both acid-catalyzed and base-catalyzed reactions with a number of functional groups, including amine groups and carboxylic acid groups, under the appropriate conditions. However, it has now been noted that epoxy crosslinking agents introduce immunogenicity to the collagen-based material as well.

Additionally, current surgical techniques include endoscopic placement of collagen-based materials in an attempt help promote healing of, for example, a tendon. However, problems with all the foregoing collagen structures include a limited tensile strength, however. This is especially a factor at the materials fixation point to bone and other tendinous structures. Thus, improved implant materials and devices are needed.

Several embodiments disclosed herein solve one or more of these problems or others. Several embodiments disclosed herein provide orthopedic devices with better biological tolerance than those currently known. In several embodiments, disclosed herein are embodiments of crosslinked collagen-based materials. In several embodiments, devices (e.g., medical devices) comprising a crosslinked collagen-based material are provided (e.g., a crosslinked collagen-based cover). In several embodiments, the collagen-based material is crosslinked using an epoxide-based crosslinking agent. In several embodiments, the toxicity of the crosslinked collagen-based material is reduced by quenching any residual crosslinking agent in the collagen matrix using a quenching agent. Several embodiments disclosed herein also address issues involving the structural integrity of devices comprising crosslinked collagen-based materials. In several embodiments, for example, a device as disclosed herein may include an underlying support structure that provides additional structural integrity to an orthopedic as disclosed herein. Several embodiments of devices disclosed herein provide reinforced collagen matrix devices with improved structural integrity and biocompatibility providing health benefits to patients in need of treatment.

Compositions

As disclosed elsewhere herein, in several embodiments, any embodiments of the reinforced collagen matrix devices or reinforced collagen matrix devices as disclosed herein can include a crosslinked collagen-based material (also referred to herein as the collagen matrix cover). In several embodiments, the crosslinked collagen-based material can be molded or cut into a suitable shape to act as a covering for a reinforced collagen matrix device (e.g., to partially, substantially, or fully cover a reinforced collagen matrix device, a suture, etc.). In several embodiments, the crosslinked collagen-based material comprises a collagenous substrate. In several embodiments, the collagenous substrate comprises collagen strands. In several embodiments, one or more collagen strands are linked together (e.g., crosslinked) by a species that spans from a first collagen strand to a second collagen strand. For example, a crosslinking agent can be used to form a crosslink that spans two collagen strands. In several embodiments, the collagenous substrate comprises a matrix of collagen strands. In several embodiments, the collagen strands (e.g., of the matrix) are crosslinked by one or more crosslinking units that bridge the strands. In several embodiments, each crosslinking unit is derived from a crosslinking agent (e.g., is formed after the reaction of a crosslinking agent with reactive groups of collagen strands during synthesis of the crosslinked collagen-based material). In several embodiments, when two or more reactive groups of a crosslinking agent react with two or more collagen strands, a crosslink between those collagen strands is provided (thereby providing the crosslinking unit).

In several embodiments, the crosslinked collagen-based material is a treated crosslinked collagen-based material. For example, as noted elsewhere herein, it has now been noted that using a quenching agent consumes residual unreacted crosslinking agent within the crosslinked collagen-based material, thereby lowering toxicity of the resultant treated crosslinked collagen-based material (versus a crosslinked collagen-based material that has not be quenched). In several embodiments, a collagen-based material of the orthopedic device comprises, consists of, or consists essentially of treated crosslinked collagen-based material.

In several embodiments, the crosslinking agent comprises a multifunctional epoxide. A multifunctional epoxide is a molecule that comprises a plurality of epoxides functional groups (e.g., 2, 3, 4, or more). In several embodiments, the multifunctional epoxide is a diepoxide. As used herein, the term "diepoxide" refers to a compound that has two reactive epoxide functionalities. Useful diepoxides may include, but are not limited to, glycol diglycidyl ether, glycerol diglycidyl ether, butanediol diglycidyl ether, resorcinol diglycidyl ether, 1,6-hexanediol diglycidyl ether, ethylene glycol diglycidyl ether, diethylene glycol diglycidyl ether, triethylene glycol diglycidyl ether, polyethylene glycol diglycidyl ether, propylene glycol diglycidyl ether, dipropylene glycol diglycidyl ether, and polybutadiene, diglycidyl ether. An example of the diepoxide that can be used to crosslink collagen strands is 1,4 butanediol digylcidyl ether (BDDGE). Multifunctional epoxides may include, but are not limited to, the above mentioned diepoxides, glycerol triglycidyl ether, sorbitol polyglycidyl ether, polyglycerol polyglycidyl ether, pentaerythritol polyglycidyl ether, diglycerol polyglycidyl ether, glycerol polyglycidyl ether, and trimethylolpropane polyglycidyl ether.

In several embodiments, the crosslinking agent comprises a structure represented by Formula (A):

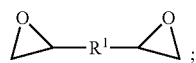

(A)

where $R^1$ as disclosed elsewhere herein. In several embodiments, $R^1$ is selected from the group consisting of optionally substituted alkylene, optionally substituted polyether, and optionally substituted polyamino. In several embodiments, $R^1$ is selected from the group consisting of optionally substituted $C_{1-6}$ alkylene, $—R_E—(N(R_A)R_B—)_n—N(R_C)—R_F—$, and $—(R_E)—(OR_B—)_nO—R_F—$, where the variables are as disclosed elsewhere herein. In several embodiments, $R^1$ is represented by a structure selected from the group consisting of: $—(CH_2)_a—(O—(CH_2)_b)_c—O—(CH_2)_d—$, $—(CH_2)_a—(NH—(CH_2)_b)_c—NH—(CH_2)_d—$, and $—(CH_2)_a—$. In several embodiments, each of a, b, c, and d is independently an integer equal to 0, 1, 2, 3, 4, 5, 6, 7, or 8. In several embodiments, $R^1$ is represented by $—CH_2—O—(CH_2)_b—O—CH_2—$ and b is 4.

In several embodiments, after crosslinking of the collagen matrix, the crosslinked collagen-based material comprises a crosslinking unit. In several embodiments, the crosslinking unit is formed through reaction with a first amine of the collagen matrix and a second amine of the collagen matrix. In several embodiments, the first amine is part of a first collagen strand of the collagenous substrate and the second amine is part of a second collagen strand of the collagenous substrate. In several embodiments, the crosslink is represented by Formula (I):

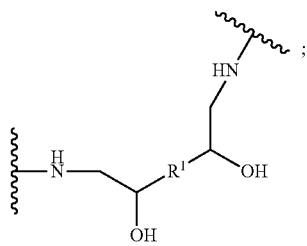

(I)

In several embodiments, $R^1$ is selected from the group consisting of optionally substituted alkylene, optionally substituted polyether, and optionally substituted polyamino. In several embodiments, $R^1$ is selected from the group consisting of optionally substituted $C_{1-6}$ alkylene, $—R_E—(N(R_A)R_B—)_n—N(R_C)—R_F—$, and $—(R_E)—(OR_B—)_nO—R_F—$, where the variables are as disclosed elsewhere herein. In several embodiments, $R^1$ is represented by a structure selected from the group consisting of: $—(CH_2)_a—(O—(CH_2)_b)_c—O—(CH_2)_d—$, $—(CH_2)_a—(NH—(CH_2)_b)_c—NH—(CH_2)_d—$, and $—(CH_2)_a—$. In several embodiments, each of a, b, c, and d is independently an integer equal to 0, 1, 2, 3, 4, 5, 6, 7, or 8. In several embodiments, $R^1$ is represented by $—CH_2—O—(CH_2)_b—O—CH_2—$ and b is 4.

In several embodiments, the crosslink of Formula (I) is further represented by Formula (Ia):

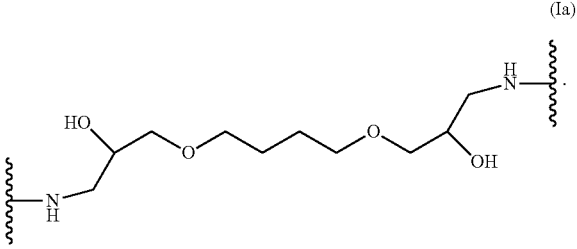 [SMILES: *NCC(O)COCCCCOCC(O)CN*]

(Ia)

In several embodiments, the crosslinking unit is formed through reaction with a carboxylic acid of the collagen matrix and an amine of the collagen matrix. In several embodiments, the carboxylic acid is part of a first collagen strand of the collagenous substrate and the amine is part of a second collagen strand of the collagenous substrate. In several embodiments, the crosslink is represented by Formula (Ic):

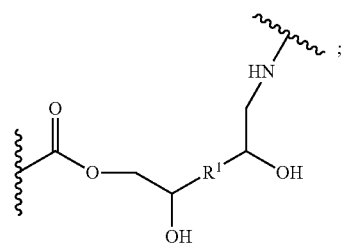

(Ic)

where $R^1$ is as disclosed elsewhere herein. In several embodiments, the variables defined for one structural formula may also be used to define that variable in any other formula having that same variable. For example, when a variable has the same alphanumeric designation (e.g., $R^1$) for one formula (e.g., Formula (I)), that definition of the variable can be used in other formulae (e.g., Formulae (Ic) or (Ia)), even where the variable is not specifically defined for those other formulae.

In several embodiments, the crosslinking unit is formed through reaction with a first carboxylic acid of the collagen matrix and a second carboxylic acid of the collagen matrix. In several embodiments, the first carboxylic acid is part of a first collagen strand of the collagenous substrate and the second carboxylic acid is part of a second collagen strand of the collagenous substrate. In several embodiments, the crosslink is represented by Formula (Id):

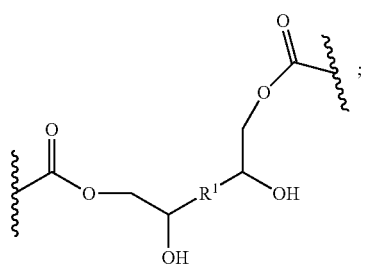

(Id)

where $R^1$ is as disclosed elsewhere herein.

As disclosed elsewhere herein, multifunctional epoxides have been used as crosslinking agents for collagen to improve physical properties of the material. However, it has now been noted that using multifunctional epoxides may lead to immunogenicity (e.g., cytotoxicity, etc.) of the crosslinked collagen material. It has now been noted that, when using epoxide crosslinking agents, epoxides of the crosslinking agent may not fully react, leaving residual epoxides present in the material. This reactive group (e.g., a residual epoxide) can be toxic and/or immunogenic. To illustrate, a crosslinked collagen material may comprise both Formula (I), (Ia), (Ic), and/or (Id) above, but at the same time may comprise units represented by Formula (Ib):

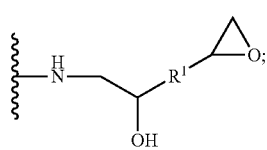

(Ib)

where $R^1$ is as described elsewhere herein. Additionally, a crosslinked collagen material may comprise both Formula (I), (Ia), (Ib), (Ic), and/or (Id) above, but at the same time may comprise units represented by Formula (Ie):

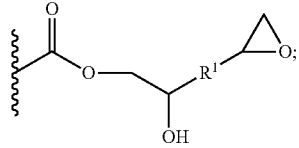

(Ie)

where $R^1$ is as described elsewhere herein.

In several embodiments, it has now been noted that using a quenching agent consumes residual epoxides, thereby lowering toxicity of the crosslinked collagen-based material. For example, a nucleophilic small molecule may be used to react with the residual epoxide groups (such as the residual epoxide shown in Formulae (Ib) and/or (Ie)). In several embodiments, the quenching group may be represented by the following formula H—$X^1$—$R^2$ where $X^1$ is a nucleophilic group. In several embodiments, $X^1$ is selected from the group consisting of —O— and —N($R^3$)—, where $R^3$ is selected from the group consisting of —H and optionally substituted $C_{1-6}$ alkyl. In several embodiments, $X^1$ is selected from the group consisting of —O— and —NH—. In several embodiments, $R^2$ is selected from the group consisting of optionally substituted alkyl, optionally substituted polyether, and optionally substituted polyamino. In several embodiments, $R^2$ is optionally substituted $C_{1-6}$ alkyl. In several embodiments, $R^2$ is —$CH_2CH_3$.

As disclosed elsewhere herein, any one or more of $R^1$, $R^2$, and $R^3$ may be optionally substituted. In several embodiments, an optional substitution may be as disclosed above. In several embodiments, when an $R^1$ group is substituted with one or more optional substitutions, the one or more optional substitutions are independently selected from the group consisting of acyl, $C_{1-6}$ alkyl, $C_{1-6}$ alkoxy, C-amido, halogen, and hydroxy. In several embodiments, when an $R^2$ group is substituted with one or more optional substitutions, the one or more optional substitutions are independently selected from the group consisting of acyl, $C_{1-6}$ alkyl, $C_{1-6}$ alkoxy, C-amido, halogen, and hydroxy. In several embodiments, when an $R^3$ group is substituted with one or more optional substitutions, the one or more optional substitutions are independently selected from the group consisting of acyl, $C_{1-6}$ alkyl, $C_{1-6}$ alkoxy, C-amido, halogen, and hydroxy.

In several embodiments, the crosslinked collagen-based material comprises a quenched crosslinking agent (e.g., by performing a quench using a quenching group as disclosed elsewhere herein). In several embodiments, the quenched crosslinking agent is bonded to the collagenous material an amine (e.g., a third amine) of the collagenous substrate. In several embodiments, the crosslinked collagen-based material comprises a structure represented by Formula (II):

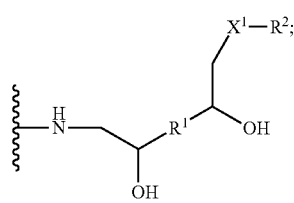

(II)

where $R^2$ and $X^1$ are as disclosed elsewhere herein. In several embodiments, $R^2$ is selected from the group consisting of optionally substituted alkyl, optionally substituted polyether, and optionally substituted polyamino. In several embodiments, $X^1$ is selected from the group consisting of —O— and —NH—. In several embodiments, $R^2$ is represented by a structure selected from the group consisting of: —$(CH_2)_a$—(O—$(CH_2)_b)_c$—O—$(CH_2)_d$—H, —$(CH_2)_a$—(NH—$(CH_2)_b)_c$—NH—$(CH_2)_d$—H, and —$(CH_2)_a$—H, where each of a, b, c, and d is independently an integer equal to 0, 1, 2, 3, 4, 5, 6, 7, or 8. In several embodiments, Formula (II) is further represented by Formula (IIa):

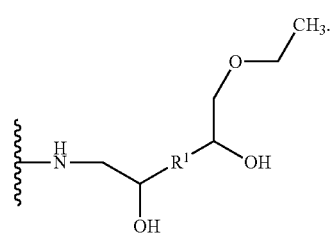

(IIa)

In several embodiments, the crosslinked collagen-based material comprises a structure represented by Formula (IIb):

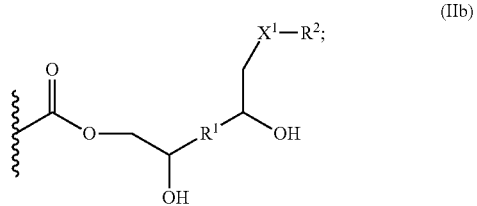

(IIb)

where $R^2$ and $X^1$ are as disclosed elsewhere herein.

In several embodiments, the crosslinked collagen-based material comprises a structure represented by any one or more of Formula (I), Formula (Ia), Formula (Ic), Formula (Id), Formula (II), Formula (IIa), Formula (IIb), and/or combinations of any of the foregoing. In several embodiments, the crosslinked collagen-based material comprises a structure represented by any one or more of Formula (I), Formula (Ia), Formula (Ic), Formula (Id), Formula (II), Formula (IIa), Formula (IIb), and/or combinations of any of the foregoing, but lacks, substantially lacks, or has a reduced amount of Formula (Ib) and/or (Ie). For example, in several embodiments, the crosslinked collagen-based material comprises a quenched crosslinking agent (e.g., prepared by performing a quench using a quenching group as disclosed elsewhere herein). In several embodiments, the quenched crosslinking agent is bonded to the collagenous material via an amine (e.g., a third amine) of the collagenous substrate. In several embodiments, the quenched crosslinking agent is bonded to the collagenous material via carboxylic acid (e.g., a third carboxylic acid) of the collagenous substrate.

In several embodiments, each instance of ∼∼∼ of Formula (I), Formula (Ia), Formula (Ib), Formula (Ic), Formula (Id), Formula (Id), Formula (II), Formula (IIa), and/or Formula (IIb) represents a portion of the collagenous substrate (e.g., a collagen strand of the collagen matrix).

In several embodiments, the crosslinked collagen-based material has desirable material properties. In several embodiments, the crosslinked collagen-based material has improved properties relative to materials that are not quenched. In several embodiments, the treated (e.g., quenched) crosslinked collagen-based material has a shrinkage temperature (Ts) equal to or at least about: 70° C., 75° C., 76° C., 77° C., 78° C., 70° C., 70° C., or ranges including and/or spanning the aforementioned values. In several embodiments, the treated crosslinked collagen-based material has a tensile strength equal to or at least about: 5 N, 7.5 N, 8.0 N, 9.0 N, 10 N, 11 N, 12 N, 15N, or ranges including and/or spanning the aforementioned values. Tensile strength can be measured using tensile bars (40.0 mm×4.0 mm×1.4 mm) cut using a dumb-bell shaped knife and can be hydrated for at least one hour in PBS at room temperature. The thickness of the samples can be measured in triplicate using a spring-loaded type micrometer. An initial gauge length of 10 mm can be used and a crosshead speed of 5 mm/minute can be applied until rupture of the test specimen occurs. A preload of 0.05 N can be applied to pre-stretch the specimen before the real measurement. In several embodiments, the treated crosslinked collagen-based material retains properties (e.g., tensile strength and/or shrinkage temperature) for a surprisingly long period of time, for example, decreasing less than 10% after a period of equal to or greater than about: 1 month, 2 months, 3 months, 4 months, 6 months, 1 year, or ranges including and/or spanning the aforementioned values.

In several embodiments, the treated crosslinked collagen-based material can be tailored to have a variable degradation rate depending on the application of the reinforced collagen matrix device. In several embodiments, the degradation rate of the treated crosslinked collagen-based material may be measured using HEPES buffered solution with a concentration of 95 mg/100 ml bacterial protease derived from *Streptomyces griseus* and an incubation time at 45° C. of 24 hours. In several embodiments, the degradation rate of the treated crosslinked collagen-based material may be measured using a pronase digestion assay. In several embodiments, the treated crosslinked collagen-based material has a degradation rate (in a pronase digestion assay as disclosed herein) per hour of less than or equal to about: 0.01%, 0.1%, 0.2%, 0.3%, 0.5%, 0.75%, 1.0%, 2.0%, or ranges including and/or spanning the aforementioned values. In several embodiments, the treated crosslinked collagen-based material has a degradation rate of between about 0.2% to about 1.0% per hour when measured using the pronase digestion assay described in the EXAMPLES section. In some embodiments, the treated crosslinked collagen-based material has a degradation rate (in a pronase digestion assay as disclose herein) that ranges from 0.1% to 1.10% (or about 0.1% to about 1.10%) per hour, from 0.3% to 1.0% (or about 0.3% to about 1.0%) per hour, from 0.4% to 0.9% (or about 0.4% to about 0.9%) per hour, from 0.5% to 0.8% (or about 0.5% to about 0.8%) per hour, from 0.6% to 0.7% (or about 0.6% to about 0.7%) per hour, from 0.2% to 0.3% (or about 0.2% to about 0.3%) per hour, from 0.3% to 0.4% (or about 0.3% to about 0.4%) per hour, from 0.4% to 0.5% (or about 0.4% to about 0.5%) per hour, from 0.5% to 0.6% (or about 0.5% to about 0.6%) per hour, from 0.6% to 0.7% (or about 0.6% to about 0.7%) per hour, from 0.7% to 0.8% (or about 0.7% to about 0.8%) per hour, from 0.8% to 0.9% (or about 0.8% to about 0.9%) per hour, from 0.9% to 1.0% (or about 0.9% to about 1.0% per hour), or from 1.0% to 1.1% (or about 1.0% to about 1.1% per hour).

Methods of Manufacture

Some embodiments provide a method of making a treated crosslinked collagen-based material. In several embodiments, the method comprises providing a collagen material. In several embodiments, the collagen material is exposed to a crosslinking solution comprising a crosslinking agent to provide a crosslinked collagen-based material. In several embodiments, the crosslinked collagen-based material is exposed to a quenching agent to provide the treated crosslinked collagen-based material. Several embodiments pertain to making a reinforced collagen matrix device by shaping the treated crosslinked collagen-based material to provide a portion of the reinforced collagen matrix device.

Figure 20:
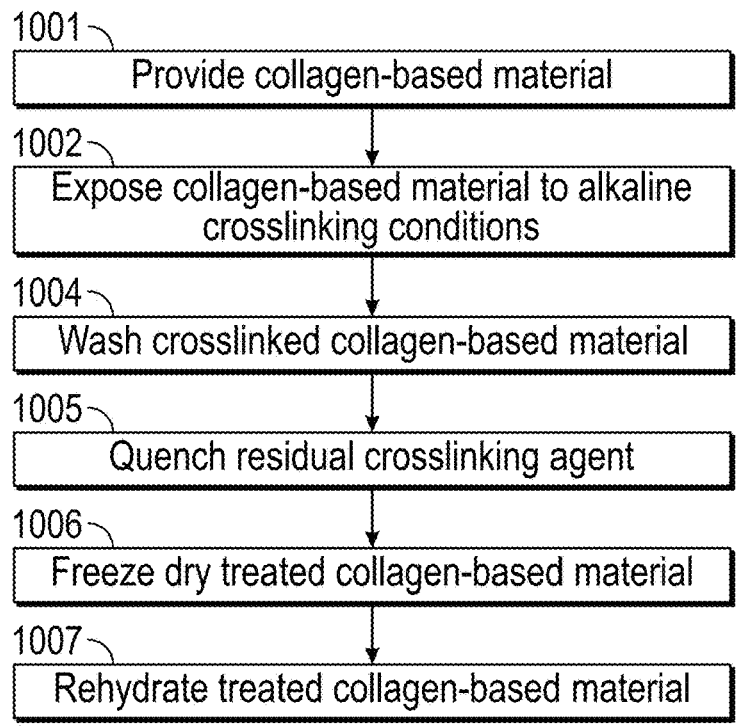
FIG. 20 is a flow chart depicting an embodiment of a method of synthesizing a crosslinked collagen-based material.
Figure 21:
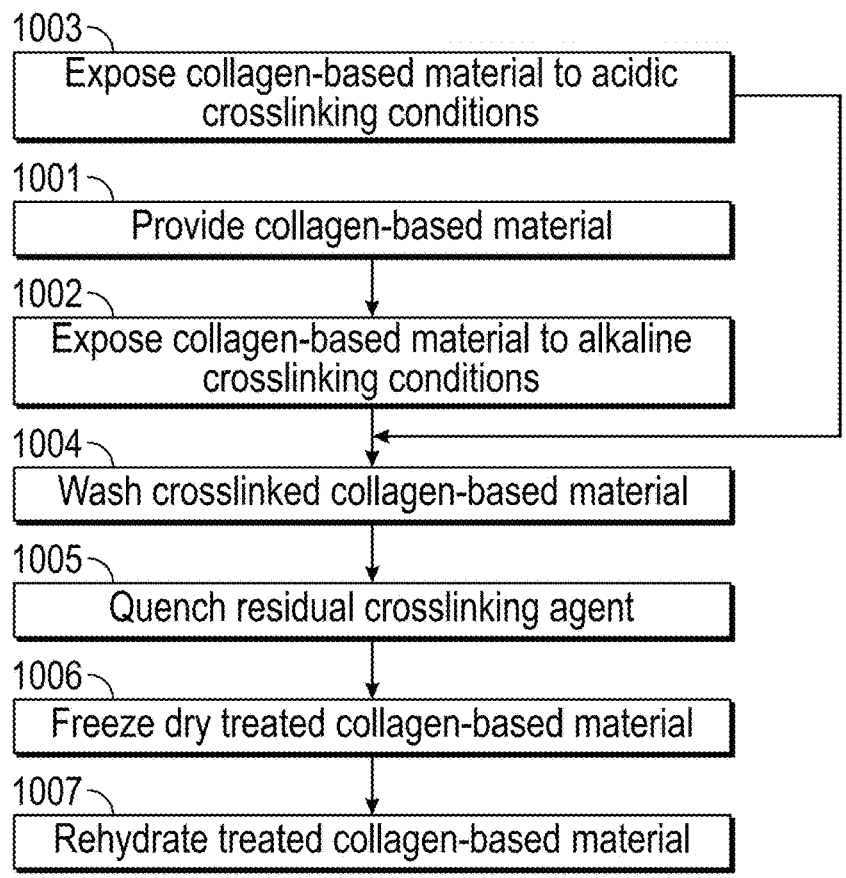
FIG. 21 is a flow chart depicting another embodiment of a method of synthesizing a crosslinked collagen-based material.

In several embodiments, as shown in FIGS. 20 and 21, the method may include a first step (1001) that includes providing a collagen-based material. In some embodiments, animal or human tissue is dissected and undergoes a decellularization process to result in the collagen-based material. In some embodiments, depending on the level of processing of natural tissue, collagen-based materials may be collagen, tropocollagen, collagen fibrils, or collagen fibers. In some embodiments, the collagen-based material is excised from the pericardium of an animal or a human. In several embodiments, collagen tissue is trimmed, cleaned of fat, debris and blood in a saline rinse. In several embodiments, the tissue is de-cellularized using sonication with an anionic surfactant (Sodium Dodecyl Sulfate) to remove a majority of intracellular materials. In several embodiments, a collagen source may include pericardium from a bovine, equine, human, or other source.

In several embodiments, as shown in FIGS. 20 and 21, the collagen-based material is exposed to solution comprising a crosslinking agent in a crosslinking step (1002). In several embodiments, the solution is a buffered solution. In several embodiments, as shown in FIGS. 20 and 21, the crosslinking step may be performed using a solution with an alkaline pH. In several embodiments, the pH is high enough to result in crosslinks that are primarily and/or exclusively amine-based. In several embodiments, the solution (e.g., buffered solution) has a pH of greater than or equal to 8.0, 8.5, 9.0, 9.2, 9.5, 10.0, 10.5, 11.0, or ranges including and/or spanning the aforementioned values. In several embodiments, the buffered solution has a pH between 8.0 to 10.5 (or about 8.0 to about 10.5). In several embodiments, the pH of the buffered solution may be from 8.9 to 9.5 (or about 8.9 to about 9.5), from 9.0 to 9.4 (or about 9.0 to about 9.4), or from 9.1 to 9.3 (or about 9.1 to about 9.3). In several embodiments, the pH of the buffered solution may be 9.2 (or about 9.2).

In several embodiments, a crosslinking agent is provided in the solution at a concentration (in w/v) of equal to or less than about: 1%, 2.5%, 5.0%, 7.5%, 10%, 12.5%, or ranges including and/or spanning the aforementioned values. In several embodiments, the crosslinking agent is provided in the solution at a concentration ranging from 1% to 10% (or from about 1% to about 10%) (w/v), from 2% to 8% (or from about 2% to about 8%) (w/v), from 3% to 7% (or about 3% to about 7%) (w/v), or from 4% to 6% (or about 4% to about 6%) (w/v). In some embodiments, the crosslinking agent concentration in the solution is 4% (or about 4%) (w/v).

In several embodiments, the collagen-based material is exposed to the alkaline crosslinking conditions (e.g., is placed in the solution comprising crosslinking agent) for a period of time to provide a crosslinked collagen-based material. In several embodiments, the crosslinking reaction is allowed to proceed for equal to or at least about: 100 hours, 140 hours, 150 hours, 152 hours, 155 hours, 157.5 hours, 160 hours, 165 hours, or ranges including and/or spanning the aforementioned values.

In several embodiments, as shown in FIG. 20 step (1001), the collagen-based material is exposed to alkaline conditions or crosslinking to achieve full crosslinking of the material. In such an embodiment, the crosslinks are primarily amine-based (e.g., involve amine groups of the collagen material). In several embodiments, as an alternative to a crosslinking reaction that occurs under only alkaline conditions (as in FIG. 20), the collagen material may also be exposed to acidic pH to achieve partial crosslinking of the collagen-based material through carboxylic acids (as shown in Step (1003) of FIG. 21 and provided in Formula (Id)).

As shown in FIG. 21, where a mixture of pH conditions is used, a first and second crosslinking step can be used. Step 1002 involves exposing the collagen-based material to a first buffered solution comprising a first crosslinking agent at a first pH for a first period of time to provide a partially crosslinked collagen-based material. In some embodiments, the first pH is high enough to result in crosslinks that are primarily amine-based. In some embodiments, the first buffered solution has a pH between 8.0 to 10.5 (or about 8.0 to about 10.5). In some embodiments, the pH of the first buffered solution may be from 8.9 to 9.5 (or about 8.9 to about 9.5), from 9.0 to 9.4 (or about 9.0 to about 9.4), or from 9.1 to 9.3 (or about 9.1 to about 9.3). In some embodiments, the pH of the first buffered solution may be 9.2 (or about 9.2). The concentration of first crosslinking agent in the first solution may be from 1% to 10% (or from about 1% to about 10%) (w/v), from 2% to 8% (or from about 2% to about 8%) (w/v), from 3% to 7% (or about 3% to about 7%) (w/v), or from 4% to 6% (or about 4% to about 6%) (w/v). In some embodiments, the first crosslinking agent concentration in the first solution is 4% (or about 4%) (w/v). The first period of time for the crosslinking reaction depends on the desired level of crosslinking, and may be from 0.5 hours to 64 hours (or about 0.5 hours to about 64 hours). In some embodiments, the first period of time may be from 1 hour to 60 hours (or about 1 hour to about 60 hours), from 10 hours to 50 hours (or about 10 hours to about 50 hours), or from 20 hours to 40 hours (or about 20 hours to about 40 hours). In some embodiments the first period of time may be from 0.5 hours to 10 hours (or about 0.5 hours to about 10 hours), from 10 hours to 20 hours (or about 10 hours to about 20 hours), from 20 hours to 30 hours (or about 20 hours to about 30 hours), from 30 hours to 40 hours (or about 30 hours to about 40 hours), from 40 hours to 50 hours (or about 40 hours to about 50 hours), from 50 hours to 60 hours (or about 50 hours to about 60 hours), or from 60 hours to 64 hours (or about 60 hours to about 64 hours). In some embodiments, the partially crosslinked collagen-based material comprises partially crosslinked collagen strands, and the crosslinks are primarily amine-based crosslinks.

Step 1003 involves exposing the collagen-based material to a second buffered solution comprising a second crosslinking agent at a low pH for a second period of time to provide a tailorably crosslinked collagen-based material. The pH of the second buffered solution is low enough to result in crosslinks that are primarily ester-based. In some embodiments, the pH of the second buffered solution may be from 3.0 to 5.5 (or about 3.0 to about 5.5). In some embodiments, the pH of the second buffered solution may be from 4.2 to 4.8 (or about 4.2 to about 4.8), from 4.3 to 4.7 (or about 4.3 to about 4.7), or from 4.4 to 4.6 (or about 4.4 to about 4.6). In some embodiments, the pH of the second buffered solution may be 4.5 (or about 4.5). The concentration of second crosslinking agent in the second solution may be from 1% to 10% (or from about 1% to about 10%) (w/v), from 2% to 8% (or from about 2% to about 8%) (w/v), from 3% to 7% (or about 3% to about 7%) (w/v), or from 4% to 6% (or about 4% to about 6%) (w/v). In some embodiments, the first crosslinking agent concentration in the first solution is 4% (or about 4%) (w/v). The second period of time for the crosslinking may be from 100 hours to 160 hours (or about 100 hours to about 160 hours). In some embodiments, the second period of time for the crosslinking may be from 100 hours to 170 hours (or about 100 hours to about 170 hours), from 110 hours to 160 hours (or about 110 hours to about 160 hours), from 120 hours to 150 hours (or about 120 hours to about 150 hours), or from 130 hours to 140 hours (or about 130 hours to about 140 hours). In some embodiments, the second period of time for the crosslinking may be from 100 hours to 110 hours (or about 100 hours to about 110 hours), from 110 hours to 120 hours (or about 110 hours to about 120 hours), from 120 hours to 130 hours (or about 120 hours to about 130 hours), from 130 hours to 140 hours (or about 130 hours to about 140 hours), from 140 hours to 150 hours (or about 140 hours to about 150 hours), from 150 hours to 160 hours (or about 150 hours to about 160 hours), or from 160 to 170 hours (or about 160 hours to about 170 hours). In some embodiments, the second period of time for the crosslinking may be performed for a period that exceeds 170 hours.

In some embodiments, for a procedure using more than one pH condition as shown in FIG. 20, the total exposure time to the first and second buffered solutions (the total of the first period of time and the second period of time) is such that the resulting tailorably crosslinked collagen-based material is substantially fully crosslinked. In some embodiments, the total exposure time will be sufficient to afford a material that contains a small enough amount of pendant free epoxides such that the material is biocompatible. In some embodiments, the sum of the first period of time and the second period of time is from 100.5 hours to 110 hours (or about 100.5 hours to about 110 hours), from 110 hours to 120 hours (or about 110 hours to about 120 hours), from 120 hours to 130 hours (or about 120 hours to about 130 hours), from 130 hours to 140 hours (or about 130 hours to about 140 hours), from 140 hours to 150 hours (or about 140 hours to about 150 hours), and/or from 150 hours to 160 hours (or about 150 hours to about 160 hours). In some embodiments, the sum of the first period of time and the second period of time is 160 hours (or about 160 hours). In some embodiments, the sum of the first and second periods of time is longer than 160 hours.

Alternatively, the pH of the buffered solutions and reaction times in steps 1002 and 1003 may be reversed in some embodiments. In some embodiments, step 1002 is performed before step 1003. In other embodiments, not shown, step 1002 may follow step 1003. The collagen-base material may be exposed to a crosslinking agent solution with a low pH first, and then a second crosslinking agent solution with a high pH second. In this case, the first buffered solution has a low pH, while the second buffered solution has a high pH. In other embodiments, as shown in FIG. 20, the low pH condition step can be omitted. For example, the crosslinking can be performed under only alkaline conditions, as shown in FIG. 20.

In some embodiments, the crosslinking agent (e.g., in steps 1002 and/or 1003) may be a diepoxide. In some embodiments, the crosslinking agent (e.g., in steps 1002 and/or 1003) is selected from the group consisting of glycol diglycidyl ether, glycerol diglycidyl ether, glycerol triglycidyl ether, and butanediol diglycidyl ether. In some embodiments, where two crosslinking conditions are used (e.g., in steps 1002 and/or 1003), the crosslinking agents in steps 1002 and/or 1003 are the same. In other embodiments, the crosslinking agents (e.g., in steps 1002 and/or 1003) may be different. In several embodiments, a plurality of crosslinking agents can be used in each crosslinking step (e.g., crosslinking agents independent selected from the group consisting of glycol diglycidyl ether, glycerol diglycidyl ether, glycerol triglycidyl ether, and butanediol diglycidyl ether). In some embodiments, where two crosslinking conditions are used (e.g., in steps 1002 and/or 1003), the crosslinking agent in both conditions is BDDGE. In several embodiments, where one crosslinking condition is used, the crosslinking agent is BDDGE. In some embodiments, the crosslinking agents (e.g., in steps 1002 and/or 1003) are water soluble, non-polymeric epoxies such as polyol polyglycidylethers.

Several embodiments of achieve a predetermined degree of crosslinking by precise control of the concentration of the crosslinking agent, the pH of the crosslinking agent, the length of time the collagen-based material is exposed to the crosslinking agent, and the temperature at which the collagen-based material is exposed to the crosslinking agent. One degree of crosslinking would be crosslinking only about 50% of the free amine or carboxyl groups which would enable the collagen material to retain sufficient resistance to premature enzymatic degradation and retain sufficient strength to complete its intended therapeutic role, yet allow the covering to ultimately dissolve, thereby avoiding a permanent implant.

Step 1004 involves isolating the tailorably crosslinked collagen-based material to provide a crosslinked collagen-based material. In several embodiments, the crosslinked material is rinsed (as shown in Step 1004 of FIGS. 20 and 21). In several embodiments, the rinse is performed in water (e.g., deionized or distilled). In several embodiments, the crosslinked collagen-based material is then rinsed with or bathed in a quenching solution (Step 1005). In several embodiments, the solution comprises a quenching group. In several embodiments, the quenching group (or quenching agent) may be represented by H—$X^1$—$R^2$ (as disclosed elsewhere herein). In several embodiments, the quenching group (e.g., quenching agent) is an alcohol. In several embodiments, the quenching agent is ethanol (e.g., where $X^1$ is —O— and $R^2$ is —$CH_2CH_3$. In several embodiments, the quenching agent is provided in a solution. In several embodiments, the quenching agent is provided in a solution of water. In several embodiments, the quenching agent is provided at a concentration in the solution of (v/v or w/v) of equal to or greater than about: 5%, 10%, 12.5%, 15%, 20%, 25%, 30%, 35%, or ranges including and/or spanning the aforementioned values. In several embodiments, after quenching, a treated crosslinked collagen-based material is provided.

In several embodiments, the treated crosslinked collagen-based material is dried (Step 1006). In several embodiments, the treated crosslinked collagen-based material is freeze dried. treated crosslinked collagen-based material is performed on final rinsed collagen in a multistep process designed to allow efficient rehydration of the material. In several embodiments, lyophilization is performed by freezing the treated crosslinked collagen-based material. In several embodiments, the temperature is ramped to <−30° C. under high vacuum and held for >1 Hour. In several embodiments, the temperature is ramped to <−20° C. under high vacuum and held for >2 Hour. In several embodiments, the temperature is ramped to <−5° C. under high vacuum and held for >1 Hour. In several embodiments, the temperature is ramped to 20°-25° C. under high vacuum and hold for >1 Hour.

In several embodiments, the treated crosslinked collagen-based material can be rehydrated after drying (as shown in Step 1007). In several embodiments, surprisingly, the treated crosslinked collagen-based material retains its material properties after rehydration. In several embodiments, once rehydrated the treated crosslinked collagen-based material is flexible and conforms to the shape of anatomical feature after to perform well in the surgical application of the material. In several embodiments, the product (e.g., treated crosslinked collagen-based material) is provided in a sheet form or assembled using a reinforcing fabric. In several embodiments, the product is the packaged in a double pouched radiation proof and moisture barrier peel pouch. In several embodiments, the treated crosslinked collagen-based material is sterilized. In several embodiments, the treated crosslinked collagen-based material is sterilized using e-beam conditions (e.g., with a dose of 20-30 kGy).

Figure 22:
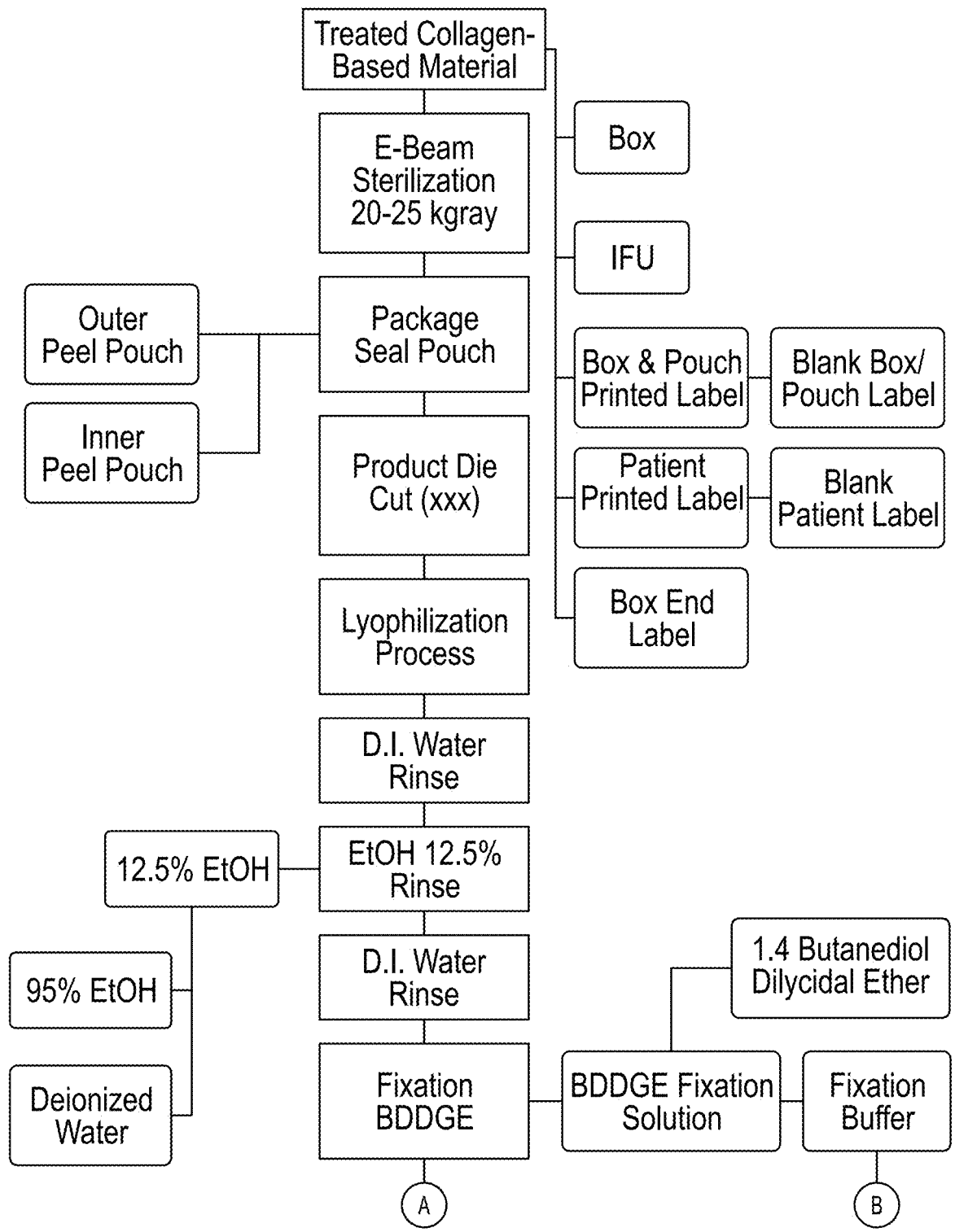
FIG. 22 is a flow chart detailing optional steps that may be used in preparing a crosslinked collagen-based material as described in FIG. 20.
Figure 22:
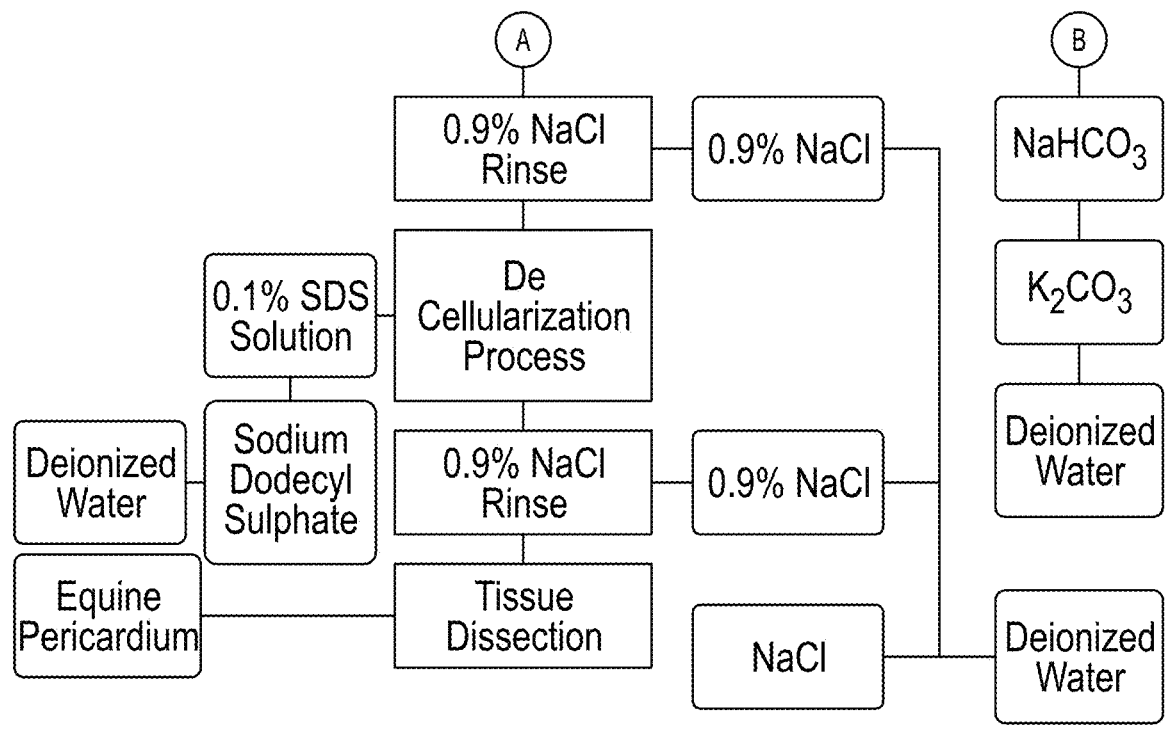
Figure 23:
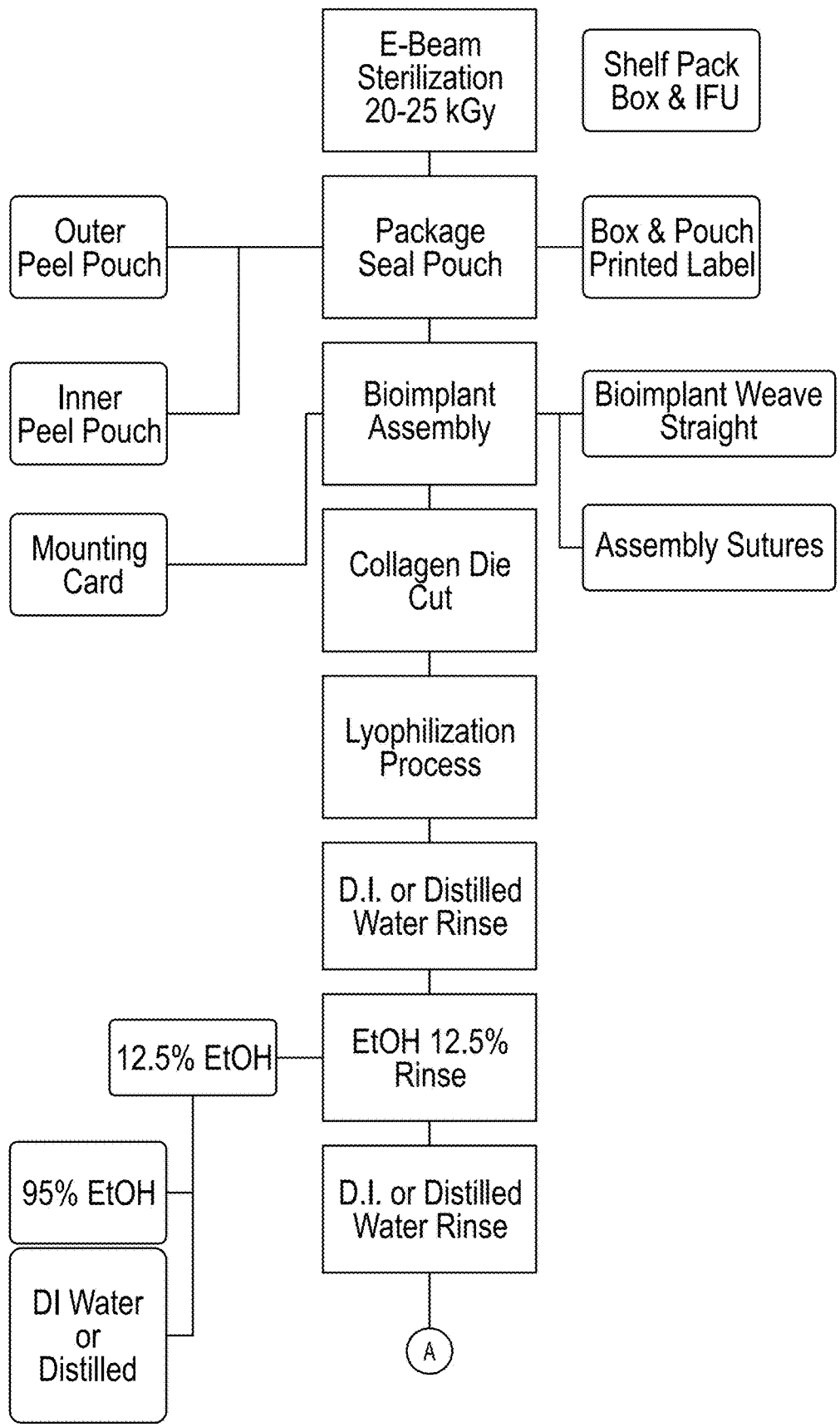
FIG. 23 is a flow chart detailing optional steps that may be used in preparing a crosslinked collagen-based material as described in FIG. 21.
Figure 23:
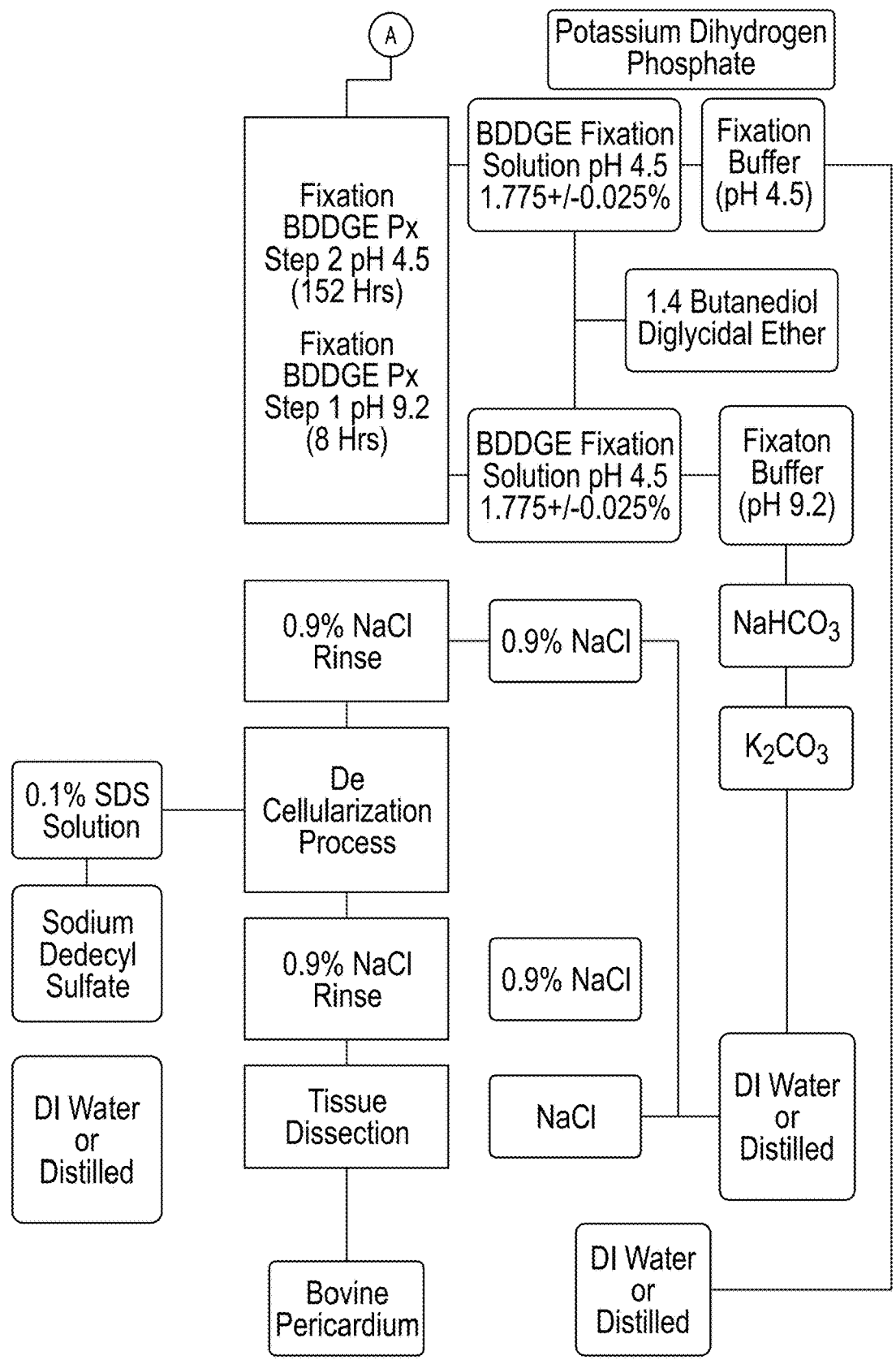

Alkaline crosslinking (e.g., of FIG. 20) provides primarily or substantially only amine based crosslinks with longer degradation times. Alkaline crosslinking may be intended for situations where long term intact collagen or implant of the device is preferable. Since the alkaline crosslinking process yields a material that is very resistant is biologic degradation it is suitable for surgical repair where natural biologic remodeling may be very slow or very long term. Examples include repair of diabetic extremity ulcers and soft tissue repair. Ester and amine crosslinked collagen matrices (as provided in FIG. 4) may be for situations where short term contact or implant of the device is preferable. Since the ester/amine process yields a material that is not as resistant to biologic degradation, it is suitable for surgical repair where biologic remodeling is considered beneficial early term. A detailed example of the manufacturing process for FIG. 20 is shown in FIG. 22. A detailed example of the manufacturing process for FIG. 21 is shown in FIG. 23.

EXAMPLES

Materials and Methods

The following is a list of materials and equipment used throughout the Examples section: Perkin Elmer Model DSC 4000, Differential Scanning Calorimeter; Boekel Scientific Oven Model 132000; Mettler Toledo Analytic Balance Model AL54; Mettler Toledo Balance New Classic ML; Calipers, Mitutoyo Corp., 505-626 Dial Caliper; Labconco Lyophilizer Model Freezone 6 with Tray Dryer; Scalpel, Bard-parker Stainless Steel Sterile blade #10; Sklar Tru-Punch, Disposable Biopsy Punch; VWR SympHony SB70P pH Meter; Distilled Water; Sodium Dodecyl Sulfate Solution 0.1%; Sonic Bath=Bransonic 2510; Equine Pericardium; 0.9% NaCl Solution; 1,4 Butanediol Diglycidyl Ether; Standard HEPES Buffer; 0.1M Phosphate Buffer pH 4.5 (purchased from Teknova; Cat. #: P4000); Fixation Buffer pH 9.2.

Preparation of Pericardium to form Collagen-Based Material

Equine pericardial sacks were procured fresh from Carnicos de Jerez S. A. de C. V. and air freighted in 0.9% NaCl solution on ice. Immediately on receipt, all sacks were rinsed in fresh, cold 0.9% NaCl solution, debrided of fat and excess fibrous tissue, and trimmed with a surgical scalpel to create 8 similar patches approximately 10 cm×15 cm. All patches were decellularized by a process of 20 minutes sonication in a 0.1% solution of Sodium Dodecyl Sulfate (SDS) followed by three separate rinses in 500 ml of 0.9% NaCl solution to remove excess SDS. The decellularization process is intended to remove any excess intracellular materials. The anionic surfactant (SDS) used in the process also helps to reduce excess fats and oils. The treatment of the resulting patches yielded debrided, decellularized pericardial patches. One of these patches was set aside as a control for crosslinking experiments. Though equine pericardial sacks were used, the pericardium of bovine specimens, humans, or other mammals may be used.

Example 1: Crosslinked Collagen-Based Material Preparation Using Low pH

To a solution phosphate buffered solution (PBS, 0.5 L, 4.5±0.2 pH) was added 1,4 butanediol diglycidyl ether (20 g) to afford a 4% by weight solution of 1,4 butanediol diglycidyl ether. This solution was stirred to yield a homogeneous solution of 4.5±0.2 pH 1,4 butanediol diglycidyl ether. This preparation provided a low pH solution of 1,4 butanediol diglycidyl ether. To the low pH solution of 1,4 butanediol diglycidyl ether (4.0% w/v 1,4 butanediol diglycidyl ether, 4.5±0.2 pH, excess) was added, an approximately 10×15 cm debrided, decellularized pericardial patch. The patch was allowed to remain in the 1,4 butanediol diglycidyl ether/PBS solution for 150-160 hours at which time the patch was rinsed with distilled water thoroughly. The patch was then rinsed with an alcohol quench solution comprising 12.5% to 25% ethanol in water. After the quench was performed, the patch was freeze dried.

Example 2: Crosslinked Collagen-Based Material Preparation Using High pH and Low pH To 1 L of deionized water was added potassium carbonate (6.5 grams) and sodium bicarbonate (16.6 grams). The solution was mixed until all solids dissolved. The pH of the solution was measured using a pH meter wherein the target pH was 9.2±0.2. If necessary, the pH of the solution was adjusted to 9.2±0.2 by adding dilute NaOH or dilute HCl. Next, to the buffered solution (bicarbonate buffer) was added 1,4 butanediol diglycidyl ether (40 g) to afford a 4% by weight solution of 1,4 butanediol diglycidyl ether. This solution was stirred to give a homogenous solution of 9.2±0.2 pH 1,4 butanediol diglycidyl ether. This preparation provided a high pH solution of 1,4 butanediol diglycidyl ether. To the high pH solution of 1,4 butanediol diglycidyl ether (4.0% w/v 1,4 butanediol diglycidyl ether, 9.2±0.2 pH, excess) was added, an approximately 10×15 cm debrided, decellularized pericardial patch. The patch was allowed to remain in the 4.0% w/v 1,4 butanediol diglycidyl ether, 9.2±0.2 pH solution for 8 hours, at which time it was added to a low pH solution of 1,4 butanediol diglycidyl ether as prepared in Example 1 (4.0% w/v 1,4 butanediol diglycidyl ether, 4.5±0.2 pH, excess). After 150-160 total crosslinking reaction time hours, the patch was removed from the low pH 1,4 butanediol diglycidyl ether solution and was rinsed with distilled water thoroughly. The patch was then rinsed with an alcohol quench solution comprising 12.5% to 25% ethanol in water. After the quench was performed, the patch was freeze dried.

Example 3: Crosslinked Collagen-Based Material Preparation Using High pH and Low pH To a high pH solution of 1,4 butanediol diglycidyl ether as prepared in Example 2 (4.0% w/v 1,4 butanediol diglycidyl ether, 9.2±0.2 pH, excess) was added, an approximately 10×15 cm debrided, decellularized pericardial patch. The patch was allowed to remain in the 4.0% w/v 1,4 butanediol diglycidyl ether, 9.2±0.2 pH solution for 24 hours, at which time it was added to a low pH solution of 1,4 butanediol diglycidyl ether as prepared in Example 1 (4.0% w/v 1,4 butanediol diglycidyl ether, 4.5±0.2 pH, excess). After 150-160 total crosslinking reaction time hours, the patch was removed from the low pH 1,4 butanediol diglycidyl ether solution and was rinsed with distilled water thoroughly. The patch was then rinsed with an alcohol quench solution comprising 12.5% to 25% ethanol in water. After the quench was performed, the patch was freeze dried.

Example 4: Crosslinked Collagen-Based Material Preparation Using High pH and Low pH To a high pH solution of 1,4 butanediol diglycidyl ether as prepared in Example 2 (4.0% w/v 1,4 butanediol diglycidyl ether, 9.2±0.2 pH, excess) was added, an approximately 10×15 cm debrided, decellularized pericardial patch. The patch was allowed to remain in the 4.0% w/v 1,4 butanediol diglycidyl ether, 9.2±0.2 pH solution for 36 hours, at which time it was added to a low pH solution of 1,4 butanediol diglycidyl ether as prepared in Example 1 (4.0% w/v 1,4 butanediol diglycidyl ether, 4.5±0.2 pH, excess). After 150-160 total crosslinking reaction time hours, the patch was removed from the low pH 1,4 butanediol diglycidyl ether solution and was rinsed with distilled water thoroughly. The patch was then rinsed with an alcohol quench solution comprising 12.5% to 25% ethanol in water. After the quench was performed, the patch was freeze dried.

Example 5: Crosslinked Collagen-Based Material Preparation Using High pH and Low pH To a high pH solution of 1,4 butanediol diglycidyl ether as prepared in Example 2 (4.0% w/v 1,4 butanediol diglycidyl ether, 9.2±0.2 pH, excess) was added, an approximately 10×15 cm debrided, decellularized pericardial patch. The patch was allowed to remain in the 4.0% w/v 1,4 butanediol diglycidyl ether, 9.2±0.2 pH solution for 48 hours, at which time it was added to a low pH solution of 1,4 butanediol diglycidyl ether as prepared in Example 1 (4.0% w/v 1,4 butanediol diglycidyl ether, 4.5±0.2 pH, excess). After 150-160 total crosslinking reaction time hours, the patch was removed from the low pH 1,4 butanediol diglycidyl ether solution and was rinsed with distilled water thoroughly. The patch was then rinsed with an alcohol quench solution comprising 12.5% to 25% ethanol in water. After the quench was performed, the patch was freeze dried.

Example 6: Crosslinked Collagen-Based Material Preparation Using High pH and Low pH To a high pH solution of 1,4 butanediol diglycidyl ether as prepared in Example 2 (4.0% w/v 1,4 butanediol diglycidyl ether, 9.2±0.2 pH, excess) was added, an approximately 10×15 cm debrided, decellularized pericardial patch. The patch was allowed to remain in the 4.0% w/v 1,4 butanediol diglycidyl ether, 9.2±0.2 pH solution for 64 hours, at which time it was added to a low pH solution of 1,4 butanediol diglycidyl ether as prepared in Example 1 (4.0% w/v 1,4 butanediol diglycidyl ether, 4.5±0.2 pH, excess). After 150-160 total crosslinking reaction time hours, the patch was removed from the low pH 1,4 butanediol diglycidyl ether solution and was rinsed with distilled water thoroughly. The patch was then rinsed with an alcohol quench solution comprising 12.5% to 25% ethanol in water. After the quench was performed, the patch was freeze dried.

Example 7: Crosslinked Collagen-Based Material Preparation Using High pH

To a high pH solution of 1,4 butanediol diglycidyl ether as prepared in Example 2 (4.0% w/v 1,4 butanediol diglycidyl ether, 9.2±0.2 pH, excess) was added, an approximately 10×15 cm debrided, decellularized pericardial patch. The patch was allowed to remain in the 4.0% w/v 1,4 butanediol diglycidyl ether, 9.2±0.2 pH solution for 150-160 hours, at which time the patch was removed from the low pH 1,4 butanediol diglycidyl ether solution and was rinsed with was rinsed with distilled water thoroughly. The patch was then rinsed with an alcohol quench solution comprising 12.5% to 25% ethanol in water.

Example 8: Drying Process

The patches prepared in Examples 1-7 were freeze-dried by lyophilization. The patches were subject to a multistage drying process. For the process, the patch was frozen in a lyophilization chamber. In the first lyophilization step the temperature was ramped to <−30° C. under high vacuum and held for >1 Hour. In the second lyophilization step the temperature was ramped to <−20° C. under high vacuum and held for >2 Hour. In the third lyophilization step the temperature was ramped to <−5° C. under high vacuum and held for >1 Hour. In the fourth lyophilization step the temperature was ramped to 20°-25° C. under high vacuum and hold for >1 Hour. The chamber and patch were then ramped to ambient temperature and pressure. Mechanical testing of a representative sample showed a tensile strength of greater than 10N with a shrinkage temperature of >76° C. Surprisingly, these dehydration conditions preserved the properties of the crosslinked collagen material (including tensile strength, shrinkage temperature, etc.). Also rehydration time in the operating room using sterile saline, flexibility & suturability. Moisture content <12% to prevent microbial growth in storage

TABLE 4

Processing of Collagen Based Material.

| | |
|---|---|
| Materials: | BDDGE Fixed Equine Pericardium (P/N 30-0001) |
| Processing: | Lyophilization Cycle Parameters |
| | Pre freeze BDDGE Fixed Pericardial Sheets to ≤−5° C. |
| | Phase 1 - Ramp to <−30° C. under high vacuum and hold for >1 Hour |
| | Phase 2 - Ramp to <−20° C. under high vacuum and hold for >2 Hour |
| | Phase 3 - Ramp to <−5° C. under high vacuum and hold for >1 Hour |
| | Phase 4 - Ramp to 20°-25° C. under high vacuum and hold for >1 Hour |
| | Phase 5 - Ramp to ambient temperature and pressure |
| Size: | Per Tissue Mounting Frame TL-0005 (Approx. 20 cm × 12 cm) |
| Appearance: | Dry and white to light yellow sheet |
| Characteristics: | Temperature of Shrinkage (DSC) Test >76° C. |
| | Tensile Strength Test >10N |

Example 9: Testing of the Crosslinked Collagen-Based Materials

1. Temperature of Shrinkage (Ts):

Three 3 mm diameter samples were cut from each of the resulting crosslinked materials from examples 1-7 and the control using a Skylar 3 mm biopsy punch. Each sample was sealed in a Perkin Elmer DSC volatile sample pan (0219-0062). An empty pan is run in parallel with the test sample in the Differential Scanning Calorimeter (DSC). Through comparison of heat flow of the empty pan and test pan, the peak temperature of enthalpy indicates the transition temperature or temperature of shrinkage (Ts) of the sample expressed in ° C. Ts of the samples are compared to that of the control or non-cross-linked to determine the comparative level of amine cross-linking present. Table 1 contains the results of each sample, separated by each example number.

TABLE 1

Temperature of Shrinkage Results (° C.)

| Sample # | 1 | 2 | 3 | Ave | SD |
|---|---|---|---|---|---|
| Example 1 | 69.63 | 70.90 | 69.71 | 70.08 | 0.58 |
| Example 2 | 72.81 | 72.40 | 72.41 | 72.54 | 0.19 |
| Example 3 | 73.91 | 74.09 | 74.19 | 74.06 | 0.12 |
| Example 4 | 76.17 | 75.98 | 76.03 | 76.06 | 0.08 |
| Example 5 | 78.31 | 78.54 | 76.53 | 78.46 | 0.11 |
| Example 8 | 77.58 | 77.11 | 76.98 | 77.22 | 0.26 |
| Example 7 | 77.26 | 77.30 | 78.21 | 77.59 | 0.44 |
| Control | 69.19 | 68.94 | 68.55 | 68.89 | 0.26 |

TABLE 1-continued

Temperature of Shrinkage Results (° C.)

| Sample # | 1 | 2 | 3 | Ave | SD |
| --- | --- | --- | --- | --- | --- |

2. Pronase Digestion Assay:

Three 1 cm×1 cm samples were cut from each of examples 1-7 and the control and tested per MF3-00X Pronase Digestion. Per procedure MF3-00X each sample was placed in a 5 ml glass scintillation vial with 4 mls of a HEPES buffered solution with 95 mg/100 ml bacterial protease derived from *Streptomyces griseus*. The samples were incubated at 45° C. for 24 hours, blotted dry and lyophilized in the Labconco lyophilizer. Then each sample was weighed utilizing the Mettler Toledo analytic balance. All samples were reweighed using the Mettler Toledo analytic balance. The percent degradation was determined calculating the percent change in weight before and after 24 hours exposure to the protease. Table 2 contains the results of each sample, separated by each example number.

TABLE 2

Protease Digestion % After 24 Hours Exposure to Protease

| | Sample # Wt (mg) after/before | | | Ave % | |
| --- | --- | --- | --- | --- | --- |
| | 1 | 2 | 3 | Remaining | SD |
| Example 1 | 5.30/7.60 | 5.40/7.30 | 5.60/7.30 | 73.47% | 2.87 |
| Example 2 | 7.80/10.10 | 8.30/10.50 | 10.60/13.20 | 78.86% | 1.26 |
| Example 3 | 10.60/11.90 | 10.80/12.20 | 12.40/13.80 | 89.15% | 0.55 |
| Example 4 | 10.50/11.90 | 11.30/12.90 | 12.70/13.90 | 89.07% | 1.65 |
| Example 5 | 14.30/14.80 | 15.70/16.00 | 19.80/20.50 | 97.11% | 0.72 |
| Example 6 | 5.00/5.40 | 6.10/6.40 | 5.10/5.50 | 93.54% | 1.25 |
| Example 7 | 11.50/12.00 | 12.10/12.60 | 12.60/12.90 | 96.51% | 0.83 |
| Control | 8.60/13.40 | 8.80/13.40 | 9.40/13.50 | 66.49% | 2.30 |

The degradation rate was then calculated by dividing the % digestion after 24 hours by 24 hours to yield % degraded/hour. Table 3 shows those results.

TABLE 3

Degradation Rate in %/hr.

| Sample # | 1 | 2 | 3 | Ave | SD |
| --- | --- | --- | --- | --- | --- |
| Example 1 | 1.26 | 1.08 | 0.97 | 1.11 | 0.15 |
| Example 2 | 0.95 | 0.87 | 0.82 | 0.88 | 0.06 |
| Example 3 | 0.46 | 0.48 | 0.42 | 0.45 | 0.03 |
| Example 4 | 0.49 | 0.52 | 0.36 | 0.46 | 0.08 |
| Example 5 | 0.14 | 0.08 | 0.14 | 0.12 | 0.04 |
| Example 6 | 0.31 | 0.20 | 0.30 | 0.27 | 0.06 |
| Example 7 | 0.17 | 0.17 | 0.10 | 0.15 | 0.04 |
| Control | 1.49 | 1.43 | 1.27 | 1.40 | 0.12 |

The study demonstrated that a pH shift from high (9.2) to low (4.5) within the first 64 hours of a 160 hour 4% 1,4 butanediol diglycidyl ether cross-linking process resulted in an extracellular collagen matrix with progressively lower Ts values, lower resistance to protease and a significantly faster bioresorbtion rate.

The process of pH modulation of the 1,4 butanediol diglycidyl ether cross-linking process of extracellular collagen matrix material is a feasible method of producing a medical device for general surgical repair with a controlled predetermined bioresorbtion rate.

3. Measuring Free Amine Content:

In addition to the tests described below, amine content can also be calculated. In some embodiments, the free amine group content of tailorably crosslinked collagen-based material, expressed as a percentage of the collagen-based material (%), can be determined using a 2,4,6-trinitrobenzenesulfonic acid (TNBS; 1.0 M solution in water, Fluka, Buchs, Switzerland) colorimetric assay. To a sample of 2-4 milligrams (mg) of tailorably crosslinked collagen-based material a solution of 1 ml of a 4% (weight/volume) aqueous NaHCO3 (pH 9.0; Aldrich, Bornem, Belgium) solution and 1 ml of a freshly prepared 0.5% (weight/volume) aqueous TNBS solution can be added. After reaction for 2 hours at 40° C., 3.0 ml of 6 M HCl (Merck, Darmstadt, Germany) can be added and the temperature can be raised to 60° C. When complete solubilization of tailorably crosslinked collagen-based material is achieved, the resulting solution is diluted with 15 ml of deionized water and the absorbance was measured on a Hewlett-Packard HP8452A UV/VIS spectrophotometer at a wavelength of 345 nm. A control is prepared applying the same procedure except that HCl was added before the addition of TNBS. The free amine group content is calculated using a molar absorption coefficient of 14600 l mol$^{-1}$ cm$^{-1}$ for trinitrophenyl lysine [Wang C. L., et al., *Biochim. Biophys. Acta*, 544, 555-567, (1978)].

The free amine group content of tailorably crosslinked collagen-based material also can be determined using a ninhydrin test. The following describes the general procedures for testing the amine content of a collagen-based material. Briefly, a sample of 1-25 milligrams (mg) of tailorably crosslinked collagen-based material is collected. Next, a solution of 1 ml of a 4% (weight/volume) ninhydrin in methyl cellosolve is prepared. Then a 0.2 M sodium citrate buffer is prepared by dissolving 1.05 g of citric acid monohydrate and 0.04 g of stannous chloride dihydrate in 11 mL of 1.0 N NaOH and adding 14 mL of purified water. The pH of the sodium citrate buffer is adjusted to 4.9 to 5.1 with HCl and/or NaOH. Next, the 4% ninhydrin solution and sodium citrate buffer are mixed in a dark bottle for immediate use. Now a solution of N-acetyllysine (ALys) is prepared by dissolving 47.1 mg of ALys in 50 mL of purified water. The ALys is used as a standard solution for calibrating the absorbance which is read at 570 nm. After a standard curve is plotted, samples of dried tissue are tested. Each solution for to be read by absorbance is prepared using 1 mL of buffered ninhydrin, 100 microliters of purified water, and the tissue or control sample. The test solutions are heated to 100° C. for 20 minutes, cooled, then 5 mL of isopropyl alcohol is added. The absorbance is then read and the amount of mols of amine per gram of sample and control is calculated from using the following equation: A=mX+b where, A=absorbance, X=content of ALys in micromoles, m=the slope, and b=the y-intercept. The content of micromoles of free amine in the sample is then $X_{samp}=(A_{samp}-b)/m$.

4. Mechanical Properties:

Stress-strain curves of the degradable bioprosthesis can be taken using uniaxial measurements using a mechanical tester. Tensile bars (40.0 mm×4.0 mm×1.4 mm) can be cut using a dumb-bell shaped knife and can be hydrated for at least one hour in PBS at room temperature. The thickness of the samples can be measured in triplicate using a spring-loaded type micrometer (Mitutoyo, Tokyo, Japan). An initial gauge length of 10 mm was used and a crosshead speed of 5 mm/minute can be applied until rupture of the test specimen occurs. A preload of 0.05 N can be applied to prestretch the specimen before the real measurement. The tensile strength, the elongation at alignment, the elongation at break, the low strain modulus and the high strain modulus of the sample can be calculated from five independent measurements.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Additionally, the phrase "consisting essentially of" will be understood to include those elements specifically recited and those additional elements that do not materially affect the basic and novel characteristics of the claimed technology. The phrase "consisting of" excludes any element not specified.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

"Treat" or "treating" or "treatment" refers to any type of action that imparts a modulating effect or therapeutic effect, which, for example, can be a beneficial effect, to a subject afflicted with an injury, disorder, disease or illness, including improvement in the condition of the subject, delay or reduction in the progression of the condition, and/or change in clinical parameters, injury or illness, curing the injury, etc. Treatment may include reduction of the symptoms of an injury or structural damage to the body (e.g., pain, reduced range of motion, stiffness, etc., resulting from an injury or damage to a joint)

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), monkeys, etc. Human subjects include neonates, infants, juveniles, adults and geriatric subjects.

Whenever a group is described as being "optionally substituted" that group may be unsubstituted or substituted with one or more of the indicated substituents. Likewise, when a group is described as being "unsubstituted or substituted" (or "substituted or unsubstituted") if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkyl(alkyl), hydroxy, alkoxy, acyl, cyano, halogen, C-carboxy, O-carboxy, nitro, sulfenyl, haloalkyl, haloalkoxy, an amino, a mono-substituted amine group, a di-substituted amine group, a mono-substituted amine(alkyl), a di-substituted amine(alkyl), a diamino-group, a polyamino, a diether-group, and a polyether-.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

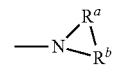

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by ⁓ followed by the number of carbon atoms, followed by a "*". For example,

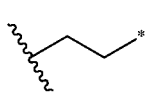

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group

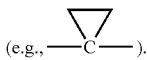

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic (such as bicyclic) hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic (such as bicyclic) hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "cycloalkyl(alkyl)" refer to a cycloalkyl group connected, as a substituent, via a lower alkylene group. The lower alkylene and cycloalkyl group of a cycloalkyl(alkyl) may be substituted or unsubstituted.

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

As used herein, a "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

An "O-carboxy" group refers to a "RC(=O)O—" group in which R can be hydrogen, an alkyl, an alkenyl, an alkynyl, a cycloalkyl, a cycloalkenyl, or cycloalkyl(alkyl), as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "nitro" group refers to an "—$NO_2$" group.

A "sulfenyl" group refers to an "—SR" group in which R can be hydrogen, an alkyl, an alkenyl, an alkynyl, a cycloalkyl, a cycloalkenyl, cycloalkyl(alkyl), or aryl(alkyl). A sulfenyl may be substituted or unsubstituted.

As used herein, "haloalkyl" refers to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The terms "amino" and "unsubstituted amino" as used herein refer to a —$NH_2$ group.

A "mono-substituted amine" group refers to a "—$NHR_A$" group in which $R_A$ can be an alkyl, an alkenyl, an alkynyl, a cycloalkyl, a cycloalkenyl, or cycloalkyl(alkyl), as defined herein. The $R_A$ may be substituted or unsubstituted. A mono-substituted amine group can include, for example, a mono-alkylamine group, a mono-$C_1$-$C_6$ alkylamine group, and the like. Examples of mono-substituted amine groups include, but are not limited to, —NH(methyl), —NH(propyl) and the like.

A "di-substituted amine" group refers to a "—$NR_AR_B$" group in which $R_A$ and $R_B$ can be independently an alkyl, an alkenyl, an alkynyl, a cycloalkyl, a cycloalkenyl, or cycloalkyl(alkyl), as defined herein. $R_A$ and $R_B$ can independently be substituted or unsubstituted. A di-substituted amine group can include, for example, a di-alkylamine group, a di-$C_1$-$C_6$ alkylamine group, and the like. Examples of di-substituted amine groups include, but are not limited to, —N(methyl)$_2$, —N(propyl)(methyl), —N(ethyl)(methyl) and the like.

As used herein, "mono-substituted amine(alkyl)" group refers to a mono-substituted amine as provided herein connected, as a substituent, via a lower alkylene group. A mono-substituted amine(alkyl) may be substituted or unsubstituted. A mono-substituted amine(alkyl) group can include, for example, a mono-alkylamine(alkyl) group, a mono-$C_1$-$C_6$ alkylamine($C_1$-$C_6$ alkyl) group, and the like. Examples of mono-substituted amine(alkyl) groups include, but are not limited to, —$CH_2$NH(methyl), —$CH_2$NH(ethyl), —$CH_2CH_2$NH(methyl), —$CH_2CH_2$NH(ethyl) and the like.

As used herein, "di-substituted amine(alkyl)" group refers to a di-substituted amine as provided herein connected, as a substituent, via a lower alkylene group. A di-substituted amine(alkyl) may be substituted or unsubstituted. A di-substituted amine(alkyl) group can include, for example, a dialkylamine(alkyl) group, a di-$C_1$-$C_6$ alkylamine($C_1$-$C_6$ alkyl) group, and the like. Examples of di-substituted amine (alkyl)groups include, but are not limited to, —$CH_2$N(methyl)$_2$, —$CH_2$N(ethyl)(methyl), —$CH_2$N(ethyl)(ethyl), —$CH_2CH_2$N(methyl)$_2$, and the like.

As used herein, the term "diamino-" denotes an a "—N($R_A$)$R_B$—N($R_C$)($R_D$)" group in which $R_A$, $R_C$, and $R_D$ can be independently a hydrogen, an alkyl, an alkenyl, an alkynyl, a cycloalkyl, a cycloalkenyl, or cycloalkyl(alkyl), as defined herein, and wherein $R_B$ connects the two "N" groups and can be (independently of $R_A$, $R_C$, and $R_D$) a substituted or unsubstituted alkylene group. $R_A$, $R_B$, $R_C$, and $R_D$ can independently further be substituted or unsubstituted.

As used herein, the term "polyamino" means a "—$R_E$—(N($R_A$)$R_B$—)$_n$—N($R_C$)($R_D$)" or a "—$R_E$—(N($R_A$)$R_B$—)$_n$—N($R_C$)—$R_F$—" group where the polyamino spans two structures. $R_A$, $R_B$, $R_C$, and $R_D$ are as disclosed elsewhere herein and $R_E$ and $R_F$ are each $C_{1-6}$ alkylene or a direct bond. For illustration, the term polyamino can comprise —$CH_2$—N($R_A$)alkyl-N($R_A$)alkyl-N($R_A$)alkyl-N($R_A$)alkyl-N($R_C$)—$CH_2CH_2$— where $R_E$ is $CH_2$, $R_B$ is alkyl, and $R_F$ is —$CH_2CH_2$—. In some embodiments, the alkyl of the polyamino is as disclosed elsewhere herein. While this example has only 4 repeat units, the term "polyamino" may consist of 1, 2, 3, 4, 5, 6, 7, 8, 9, or 10 repeat units (e.g., n may be 1, 2, 3, 4, 5, 6, 7, 8, 9, or 10). $R_A$, $R_C$, and $R_D$, where present, can be independently a hydrogen, an alkyl, an alkenyl, an alkynyl, or a cycloalkyl, as defined herein, and wherein $R_B$ connects the two "N" groups and can be (independently of $R_A$, $R_C$, and $R_D$) a substituted or unsubstituted alkylene group. $R_A$, $R_C$, and $R_D$ can independently further be substituted or unsubstituted. As noted here, the polyamino comprises amine groups with intervening alkyl groups (where alkyl is as defined elsewhere herein).

As used herein, the term "polyether" denotes a repeating —$R_E$—(O$R_B$—)$_n$O$R_D$ group or a "—($R_E$)—(O$R_B$—)$_n$O—$R_F$—" group where the polyether spans two structures. $R_B$, $R_D$, $R_E$, and $R_F$ are as disclosed elsewhere herein. For instance, $R_E$ and $R_F$ may each be $C_{1-6}$ alkylene or a direct bond. For illustration, the term polyether can comprise —Oalkyl-Oalkyl-Oalkyl-Oalkyl-O$R_A$. For further illustration, the term polyether can comprise —$CH_2$—Oalkyl-Oalkyl-O—$CH_2CH_2$— where $R_E$ is $CH_2$, $R_B$ is alkyl, and $R_F$ is —$CH_2CH_2$—. In some embodiments, the alkyl of the polyether is as disclosed elsewhere herein. While this example has only 2 repeat units, the term "polyether" may consist of 1, 2, 3, 4, 5, 6, 7, 8, 9, or 10 repeat units (e.g., n may be 1, 2, 3, 4, 5, 6, 7, 8, 9, or 10). $R_D$ can be a hydrogen, an alkyl, an alkenyl, an alkynyl, a cycloalkyl, or a cycloalkenyl, as defined herein. $R_B$ can be a substituted or unsubstituted alkylene group. $R_A$ can independently further be substituted or unsubstituted. As noted here, the polyether comprises ether groups with intervening alkyl groups (where alkyl is as defined elsewhere herein and can be optionally substituted).

Where the number of substituents is not specified (e.g. haloalkyl), there may be one or more substituents present. For example, "haloalkyl" may include one or more of the same or different halogens.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, the term "collagen strand" refers to tropocollagen, collagen fibrils and/or collagen fibers. Collagenous substrates (e.g., collagen substrates) may comprise a matrix of collagen strands. Collagen strands have pendant amine (—$NH_2$) and carboxylic acid (—COOH) groups which are reactive (e.g., to crosslinking agents). These amines and carboxylic acid groups are readily crosslinked between collagen strands with various crosslinking agents to form structures with improved medial properties. Crosslinking can be performed by taking advantage of pendant reactive groups on the collagen strand.

As used herein, the term "degradation time" refers to the amount of time it takes for a collagen-based material to completely degrade or to degrade to such an extent that it no longer serves the purpose for which it was medically intended. When degradation times are provided herein, those degradation rates may be performed under conditions described in the Examples, for example, under pronase degradation conditions.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A reinforced collagen matrix device for tendon and ligament repair, comprising: a collagen matrix cover having a length extending between a first end and a second end, a first fold adjacent to a first side of the cover, and a second fold adjacent to a second side of the cover; a first reinforcement strip positioned along the first side of the cover, the first reinforcement strip comprising a first surface and an opposite second surface; and a second reinforcement strip positioned along the second side of the cover, the second reinforcement strip comprising a first surface and an opposite second surface; a first suture coupling the first reinforcement strip to the collagen matrix cover, the first suture extending through the collagen matrix cover and the first reinforcement strip; wherein: the first reinforcement strip has a length that is greater than the length of the collagen matrix cover such that a first end and a second end of the first reinforcement strip extend past the first end and the second end of the collagen matrix cover and are not covered by the collagen matrix cover; the first reinforcement strip has a width that is substantially greater than a thickness of the first reinforcement strip; the collagen matrix cover is folded along the first fold and extends over the first reinforcement strip so that the first surface and the second surface of the first reinforcement strip are covered by the collagen matrix cover along a portion of the length of the first reinforcement strip; the second reinforcement strip has a length that is greater than the length of the collagen matrix cover such that a first end and a second end of the second reinforcement strip extend past the first and the second ends of the collagen matrix cover and are not covered by the collagen matrix cover; the second reinforcement strip has a width that is substantially greater than a thickness of the second reinforcement strip; and the collagen matrix cover is folded along the second fold and extends over the second reinforcement strip so that the first surface and the second surface of the second reinforcement strip are covered by the collagen matrix cover along a portion of the length of the second reinforcement strip.

2. The reinforced collagen matrix device of claim 1, wherein the collagen matrix cover has a trapezoidal shape after folding the collagen matrix cover along the first and second folds.

3. The reinforced collagen matrix device of claim 2, wherein the collagen matrix cover has a first end edge that is approximately 1.6 times longer than a second, opposite end edge and one or more side edges that are approximately 1.6 times longer than the first end edge.

4. The reinforced collagen matrix device of claim 1, further comprising at least four bone anchors, wherein the reinforced collagen matrix device is configured to be anchored to the patient using the at least four bone anchors, and wherein one bone anchor is used for each of the first end portion of the first reinforcement strip, the second end portion of the first reinforcement strip, the first end portion of the second reinforcement strip, and the second end portion of the second reinforcement strip.

5. The reinforced collagen matrix device of claim 1, wherein the first suture extends through two layers of the collagen matrix cover and the first reinforcement strip that is positioned between the two layers of the collagen matrix cover, wherein the first suture comprises multiple lines of sutures extending along the length of the collagen matrix cover.

6. The reinforced collagen matrix device of claim 1, wherein the reinforcement strips are at least twice as long as the collagen matrix cover.

7. The reinforced collagen matrix device of claim 1, wherein the collagen matrix cover has an ovoidal shape or triangular shape.

8. The reinforced collagen matrix device of claim 1, wherein the collagen matrix cover is configured to be cut in an anatomical shape to match a shape of a natural tendinous structure requiring surgical repair.

9. The reinforced collagen matrix device of claim 1, wherein the collagen matrix cover covers an entire periphery of the first and second reinforcement strips along a length of the first and the second reinforcement strips that overlap the collagen matrix cover.

10. The reinforced collagen matrix device of claim 1, wherein the collagen matrix cover has a first end edge that is approximately 1.6 times longer than a second, opposite end edge.

11. The reinforced collagen matrix device of claim 1, wherein the collagen matrix cover comprises at least one channel or cut having a reduced thickness along at least the first fold, the reduced thickness being less than a thickness of the collagen matrix cover adjacent to the at least one channel.

12. The reinforced collagen matrix device of claim 11, wherein the reduced thickness is approximately 0.1 mm, and the thickness of the collagen matrix cover adjacent to the at least one channel is approximately 0.5 mm, or wherein the reduced thickness of the channel is from 10% to 50% of the thickness of the collagen matrix cover adjacent to the at least one channel.

13. The reinforced collagen matrix device of claim 1, wherein the collagen matrix cover comprises:
a collagenous substrate comprising collagen strands, a crosslink, and a quenched crosslinking agent;
wherein the crosslink comprises a crosslinking unit, a first amine, and a second amine, the first amine being part of a first collagen strand of the collagenous substrate and the second amine being part of a second collagen strand of the collagenous substrate, the crosslink being represented by Formula (I):

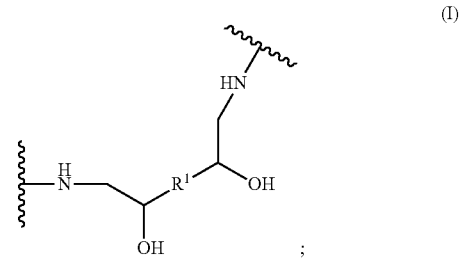

wherein the quenched crosslinking agent is bonded to the collagenous material through a third amine of the collagenous substrate and is represented by Formula (II):

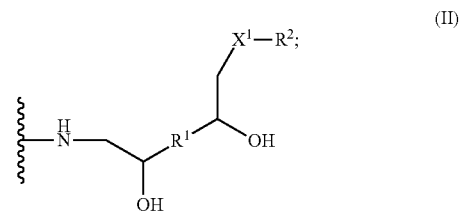

where
$R^1$ is selected from the group consisting of optionally substituted alkylene, optionally substituted polyether, and optionally substituted polyamino;
$R^2$ is selected from the group consisting of optionally substituted alkylene, optionally substituted polyether, and optionally substituted polyamino;
$X^1$ is selected from the group consisting of —O— and —NH—
where each instance of " ⁓⁓⁓ " of Formulae (I) and (II) represents a portion of the collagenous substrate.

14. The reinforced collagen matrix device of claim 13, wherein the $R^1$ is represented by a structure selected from the group consisting of: —$(CH_2)_a$—$(O$—$(CH_2)_b)_c$—$O$—$(CH_2)_d$—, —$(CH_2)_a$—$(NH$—$(CH_2)_b)_c$—$NH$—$(CH_2)_d$—, and —$(CH_2)_a$—, where each of a, b, c, and d is independently an integer equal to 0, 1, 2, 3, 4, 5, 6, 7, or 8.

15. The reinforced collagen matrix device of claim 13, where $R^1$ is represented by —$CH_2$—$O$—$(CH_2)_b$—$O$—$CH_2$— and b is 4.

16. The reinforced collagen matrix device of claim 13, wherein the crosslink is further represented by Formula (Ia):

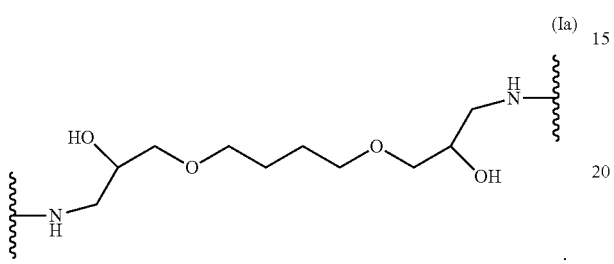

(Ia)

17. The reinforced collagen matrix device of claim 13, wherein the $R^2$ is represented by a structure selected from the group consisting of: —$(CH_2)_a$—$(O$—$(CH_2)_b)_c$—$O$—$(CH_2)_d$—H, —$(CH_2)_a$—$(NH$—$(CH_2)_b)_c$—$NH$—$(CH_2)_d$—H, and —$(CH_2)_a$—H, where each of a, b, c, and d is independently an integer equal to 0, 1, 2, 3, 4, 5, 6, 7, or 8.

18. The reinforced collagen matrix device of claim 13, wherein the quenched crosslinking agent is represented by Formula (IIa):

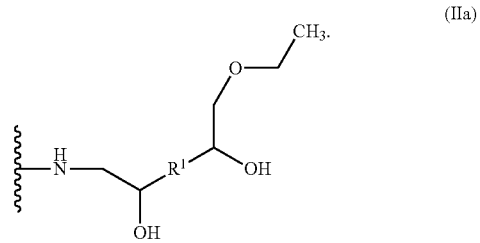

(IIa)

19. The reinforced collagen matrix device of claim 1, wherein the first and second reinforcement strips are made of a polymeric surgical mesh material.

20. The reinforced collagen matrix device of claim 1, further comprising a second suture coupling the second reinforcement strip to the collagen matrix cover, the second suture extending through the collagen matrix cover and the second reinforcement strip.

* * * * *